(12) United States Patent
    Tashiro

(10) Patent No.: US 11,517,201 B2
(45) Date of Patent: Dec. 6, 2022

(54) PHOTOACOUSTIC IMAGE GENERATION APPARATUS AND OPERATION METHOD OF PHOTOACOUSTIC IMAGE GENERATION APPARATUS

(71) Applicant: FUJIFILM Corporation, Tokyo (JP)

(72) Inventor: Rika Tashiro, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 225 days.

(21) Appl. No.: 16/811,159

(22) Filed: Mar. 6, 2020

(65) Prior Publication Data

US 2020/0205671 A1    Jul. 2, 2020

Related U.S. Application Data

(63) Continuation of application No. PCT/JP2018/024143, filed on Jun. 26, 2018.

(30) Foreign Application Priority Data

Sep. 8, 2017 (JP) .............................. JP2017-173552

(51) Int. Cl.
    *A61B 5/00*      (2006.01)
    *A61B 5/06*      (2006.01)
    *A61B 8/00*      (2006.01)
    *A61B 8/08*      (2006.01)
    *A61B 10/02*     (2006.01)

(52) U.S. Cl.
    CPC .......... *A61B 5/0095* (2013.01); *A61B 5/0035* (2013.01); *A61B 5/061* (2013.01);
    (Continued)

(58) Field of Classification Search
    CPC ..... A61B 5/0095; A61B 5/0035; A61B 5/061; A61B 5/6848; A61B 8/462; A61B 8/463;
    (Continued)

(56) References Cited

U.S. PATENT DOCUMENTS

| 5,330,443 A  * | 7/1994 | Powles .............. A61B 10/0283 600/583 |
| 2014/0081142 A1* | 3/2014 | Toma .................. A61B 8/4245 600/443 |

(Continued)

FOREIGN PATENT DOCUMENTS

| JP | 2005-58584 A | 3/2005 |
| JP | 2005-323669 A | 11/2005 |

(Continued)

OTHER PUBLICATIONS

International Preliminary Report on Patentability and Written Opinion of the International Searching Authority with an English translation (forms PCT/IB/373, PCT/ISA/237 and PCT/IB/326), dated Mar. 19, 2020, for corresponding International Application No. PCT/JP2018/024143.

(Continued)

*Primary Examiner* — Joseph M Santos Rodriguez
(74) *Attorney, Agent, or Firm* — Birch, Stewart, Kolasch & Birch, LLP

(57) ABSTRACT

In a photoacoustic image generation apparatus and an operation method of the photoacoustic image generation apparatus, all positions of an insert during puncture can be accurately grasped on an image after an examination. A photoacoustic image generation apparatus includes a photoacoustic image generation unit that generates a photoacoustic image based on a detection signal acquired by detecting a photoacoustic wave emitted from a tip portion of an insert inserted into a subject using acoustic wave detection means, and a control unit that causes a storage unit to store position information of the tip portion of a puncture needle on the photoacoustic image in response to a predetermined trigger during a step of collecting a cell of the subject at the tip portion of the puncture needle in cytology.

20 Claims, 28 Drawing Sheets

(52) U.S. Cl.
CPC ............ *A61B 5/6848* (2013.01); *A61B 8/463* (2013.01); *A61B 8/0841* (2013.01); *A61B 8/5261* (2013.01); *A61B 8/54* (2013.01); *A61B 10/0283* (2013.01)

(58) Field of Classification Search
CPC ..... A61B 8/543; A61B 8/0841; A61B 8/5261; A61B 8/54; A61B 10/0283; A61B 8/488; A61B 8/5246; G01S 7/52073; G01S 7/52074; G01S 15/899
See application file for complete search history.

(56) References Cited

U.S. PATENT DOCUMENTS

2015/0201906 A1* 7/2015 Yoshida ................ A61B 8/0841
600/424
2016/0270764 A1* 9/2016 Wodecki ................ A61B 8/462

FOREIGN PATENT DOCUMENTS

| JP | 2012-70837 | A | 4/2012 | | |
| JP | 2012-120747 | A | 6/2012 | | |
| JP | 2015-136494 | A | 7/2015 | | |
| JP | 2015-231583 | A | 12/2015 | | |
| JP | 2016-64010 | A | 4/2016 | | |
| JP | 2016064010 | | * 12/2020 | ........... | A61B 5/0095 |

OTHER PUBLICATIONS

International Search Report (form PCT/ISA/210), dated, Sep. 11, 2018, for corresponding International Application No. PCT/JP2018/024143, with an English translation.

Japanese Office Action for corresponding Japanese Application No. 2019-540781, dated Mar. 16, 2021, with English translation.

* cited by examiner

FIG. 7
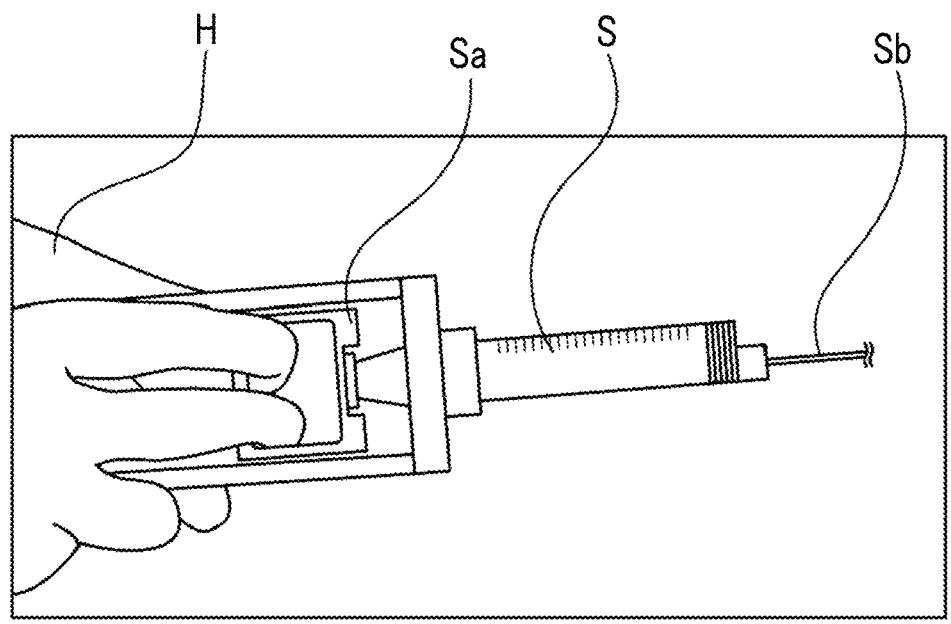
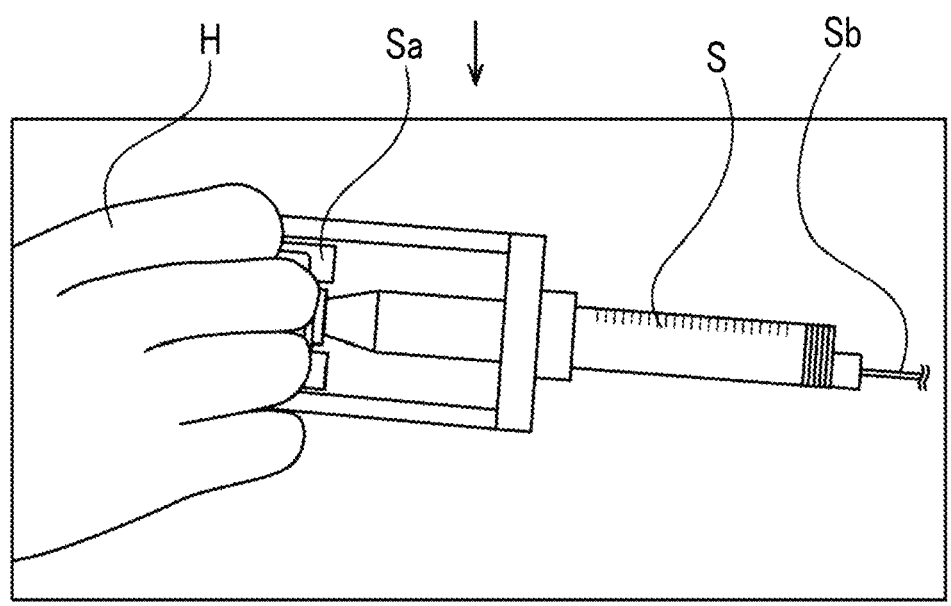

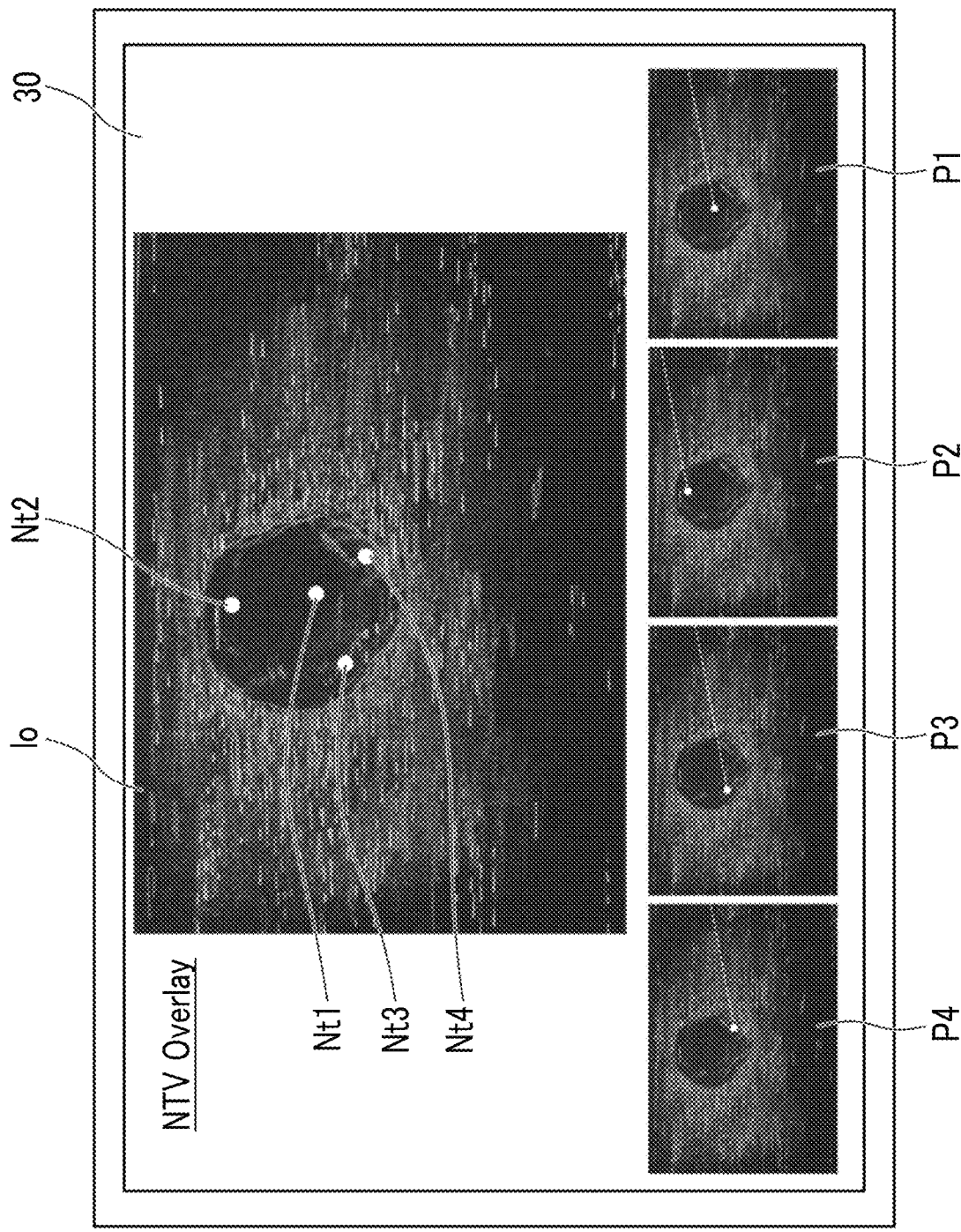

PHOTOACOUSTIC IMAGE GENERATION APPARATUS AND OPERATION METHOD OF PHOTOACOUSTIC IMAGE GENERATION APPARATUS

CROSS REFERENCE TO RELATED APPLICATIONS

This application is a Continuation of PCT International Application No. PCT/JP2018/024143 filed on Jun. 26, 2018, which claims priority under 35 U.S.C § 119(a) to Patent Application No. 2017-173552 filed in Japan on Sep. 8, 2017, all of which are hereby expressly incorporated by reference into the present application.

BACKGROUND OF THE INVENTION

1. Field of the Invention

The present invention relates to a photoacoustic image generation apparatus that generates a photoacoustic image based on a detection signal acquired by detecting a photoacoustic wave emitted from a tip portion of an insert inserted into a subject using acoustic wave detection means and an operation method of the photoacoustic image generation apparatus.

2. Description of the Related Art

An ultrasonography method is known as a kind of image examination method that can non-invasively examine an internal state of a living body. An ultrasound probe that can transmit and receive ultrasonic waves is used in ultrasonography. In a case where the ultrasound probe transmits an ultrasonic wave to a subject (living body), the ultrasonic wave travels inside the living body and is reflected from an interface between tissues. The ultrasound probe receives the reflected ultrasonic wave and a distance is calculated based on a time until the reflected ultrasonic wave returns to the ultrasound probe. In this manner, it is possible to capture an image indicating the internal state of the living body.

In addition, photoacoustic imaging is known in which an image of the inside of a living body is captured using a photoacoustic effect. In general, the inside of the living body is irradiated with pulsed laser light in the photoacoustic imaging. In the inside of the living body, the living body tissue absorbs energy of the pulsed laser light and an ultrasonic wave (photoacoustic wave) is generated by adiabatic expansion caused by the energy. The ultrasound probe or the like detects the photoacoustic wave and a photoacoustic image is formed based on the detection signal. In this manner, it is possible to visualize the inside of the living body based on the photoacoustic wave. As a technique related to the photoacoustic imaging, JP2015-231583A discloses a puncture needle provided with a photoacoustic wave generation portion that absorbs light and generates a photoacoustic wave near a tip thereof. In the puncture needle, an optical fiber is provided up to the tip of the puncture needle and light guided by the optical fiber is emitted to the photoacoustic wave generation portion. An ultrasound probe detects the photoacoustic wave generated by the photoacoustic wave generation portion, and a photoacoustic image is generated based on the detection signal of the photoacoustic wave. A portion of the photoacoustic wave generation portion appears as a bright point in the photoacoustic image. Therefore, it is possible to check a position of the puncture needle using the photoacoustic image.

On the other hand, pathological diagnosis methods for lesions are classified into cytodiagnosis (hereinafter referred to as cytology) and histological diagnosis (hereinafter referred to as histology). The cytology is a diagnostic method of collecting a cell such as a specimen or a secretion from a suspected organ with a lesion to determine the presence or absence of an atypical cell, a so-called cancer cell, in the collected specimen, in a case where there is a possibility that the lesion exists in an image diagnosis using a medical image acquired by capturing a radiographic image or an ultrasound image of a patient.

As shown in Table 1 below, there are three types of cytology according to a specimen collection method: peeling cytology, scratch cytology, and fine needle aspiration cytology. In general, the peeling cytology is adopted to a lung cancer examination in which sputum is collected and to bladder cancer and ureteral cancer examinations in which urine is collected to perform the cytology. The scratch cytology is adopted to a uterine cancer examination in which uterine mucosa is scratched with a cotton swab or the like to collect a cell. The fine needle aspiration cytology is adopted to a breast cancer examination in which an elongated needle used for blood collection is punctured into a lesion portion to collect a cell to perform the cytology.

TABLE 1

| Cytology Type | Content |
| --- | --- |
| Peeling Cytology | Method of examining a cell included in fluid such as pleural effusion, ascites, cerebrospinal fluid, pericardial fluid, pancreatic juice, or bile in addition to naturally discharged fluid such as urine or sputum. |
| Scratch Cytology | Method of examining a cell collected by actively scratching the cell with a brush or a cotton swab without waiting for a cell being peeled off, for uterine cervix, uterine body, bronchi, or the like in many cases. |
| Fine Needle Aspiration Cytology | Method of examining a cell collected by puncturing an elongated needle into a lesion portion, such as mammary gland, thyroid gland, or lymph node, that cannot be touched with a brush or a cotton swab. |

In the cytology, an examination result is determined by class as shown in Table 2 below, and it is determined that there is a cancer cell, that is, there is a suspicion of cancer in a case where the examination result is class III or higher.

TABLE 2

| Class | Content |
| --- | --- |
| Class I | There is no atypical cell. |
| Class II | Atypical cell is present, but there is no suspicious of malignancy. |
| Class III | Atypical cell is present, but malignancy cannot be determined. |
| Class IV | There is atypical cell with strong suspicious of malignancy. |
| Class V | There is atypical cell that can be determined to be malignant. |

In a case where it is determined that the cancer is suspected in the cytology, the histology is performed to confirm the suspicion of cancer, that is, to diagnose whether an atypical cell is malignant. The histology is an examination performed in a case where the cancer cannot be confirmed by the cytology or in a case where a treatment policy such as the necessity of surgery is decided. In the histology, a tissue of a lesion containing a wide range of cells is collected with a scalpel or biopsy needle and the collected tissue is observed with a microscope to diagnose the cancer malignancy, type, or the like.

In the histology, a degree of invasiveness to the patient is relatively high since the lesion tissue of the patient is cut out, and it takes time to collect the tissue since anesthesia is required. On the contrary, in the cytology, for example, in the above fine needle aspiration cytology, the degree of invasiveness to the patient is low compared with the histology since the cell collection is performed by a thin needle for blood collection, that is, an injection needle, and the time required for cell collection is also short since the anesthesia is usually unnecessary. Therefore, the cytology is widely performed before the histology is performed in recent years.

SUMMARY OF THE INVENTION

In the above histology and fine needle aspiration cytology (FNA) using the biopsy needle, an ultrasound probe is held by one hand and the needle is operated by the other hand as shown in FIG. 5. Therefore, detailed operation of an ultrasound diagnostic apparatus during puncture is difficult. Therefore, an appropriate image or video frame is selected from a plurality of saved image lists after the examination, and assignment of an annotation such as an arrow or the like is performed to indicate a punctured position. This is troublesome for an operator. The thin needle such as the injection needle is used instead of a thick needle such as the biopsy needle and thus is not clearly drawn on the image particularly in the case of FNA. Therefore, it is difficult to find a position of the needle clearly on the image later. In general, a needle tip is moved a plurality of times in one lesion portion in the FNA. Therefore, the presence of the needle may be difficult to view due to tissue damage and thus it is difficult to find a position of the needle clearly on the image later.

JP2012-120747A and JP2012-070837A disclose that a history of past needle tip positions is displayed as an image. However, in JP2012-120747A and JP2012-070837A, a needle tip is detected in a case where the needle moves in a subject without using photoacoustic imaging, and the needle tip cannot be detected in a case where the needle does not move in the subject. Therefore, in a case where the fine needle aspiration cytology is performed, it may be difficult to detect an accurate position of the needle tip in a case where a cell is aspirated in a state where a puncture needle is stationary in the subject. JP2005-058584A, JP2005-323669A, and JP2015-136494A are documents relating to puncture support for volume data in a case where histology or puncture needle ablation is performed respectively, and disclose saving and displaying a position of a needle tip. However, the photoacoustic imaging is not used and there is no description of the cytology in the documents.

The invention is made in view of such problems, and an object of the invention is to provide a photoacoustic image generation apparatus and an operation method of the photoacoustic image generation apparatus capable of accurately grasping a position of an insert during puncture on an image after an examination in a case where cytology is performed.

The photoacoustic image generation apparatus according to an embodiment of the invention comprises a photoacoustic image generation unit that generates a photoacoustic image based on a detection signal acquired by detecting a photoacoustic wave emitted from a tip portion of an insert inserted into a subject using acoustic wave detection means, and a control unit that responds to a predetermined trigger to cause storage means to store position information of the tip portion of the insert on the photoacoustic image for each trigger during a step of collecting a cell of the subject at the tip portion of the insert in cytology.

Here, in the invention, "position information" means information that can be used to detect the position of the tip portion of the insert. For example, only a still image of a real-time photoacoustic image generated by the photoacoustic image generation unit may be used as the position information. Alternatively, a position of the tip portion of the insert on a coordinate may be detected from the still image, and the detected coordinate value may be used as the position information. The still image and the coordinate value may be combined as the position information.

The photoacoustic image generation apparatus according to the embodiment of the invention may further comprise an input unit to which the predetermined trigger is input.

In the photoacoustic image generation apparatus according to the embodiment of the invention, the control unit may generate the predetermined trigger in a case where a position of the tip portion of the insert on the photoacoustic image does not move more than a predetermined distance within a predetermined time.

In the photoacoustic image generation apparatus according to the embodiment of the invention, the control unit may generate the predetermined trigger in a case where a direction in which a position of the tip portion of the insert on the photoacoustic image changes over time is switched from one direction to another direction.

Here, in the invention, "in a case of switching from one direction to another direction" means that a direction of movement in a case where the insert moves is one direction and a direction different from the one direction is another direction.

In the photoacoustic image generation apparatus according to the embodiment of the invention, the control unit may assign identification information to the position information stored for each trigger.

In the invention, the "identification information" may be different marker information, color-specific information, or number information as long as each piece of position information can be identified.

The photoacoustic image generation apparatus according to the embodiment of the invention further comprises an ultrasound image generation unit that generates an ultrasound image based on a detection signal acquired by detecting a reflected acoustic wave with respect to an ultrasonic wave output into the subject using the acoustic wave detection means, and an image display unit that displays at least one of the photoacoustic image or the ultrasound image. The image display unit may be able to perform a two-screen display. The control unit may display an overlaid image obtained by overlaying the ultrasound image and the photoacoustic image in real time on one screen of the image display unit and display a representative image on the other screen.

Here, in the invention, the "representative image" may be, for example, an ultrasound image on which a still image of a photoacoustic image is overlaid or an image acquired in advance and stored in a server or the like as long as the image is an image representing the subject, that is, the same patient. The "representative image" may be a still image, a video, a two-dimensional image, or a three-dimensional image, and is not particularly limited. The user can randomly set or change.

In the photoacoustic image generation apparatus according to the embodiment of the invention, the representative image may be a cross-sectional image in a longitudinal direction and a cross-sectional image in a transverse direction. The control unit may cause the image display unit to display the cross-sectional image in the longitudinal direction and the cross-sectional image in the transverse direction side by side.

Here, in the invention, the "longitudinal direction" and the "transverse direction" are directions perpendicular to each other in the subject. For example, in a case where the subject is a human body, a height direction may be the longitudinal direction and a direction perpendicular to the height direction may be the transverse direction.

In the photoacoustic image generation apparatus according to the embodiment of the invention, the control unit may output an accumulated image of the position information stored for each trigger to display means.

In the invention, the "accumulated image" means an image indicating the position of the tip portion of the insert stored for each trigger on one image.

In the photoacoustic image generation apparatus according to the embodiment of the invention, the insert may have an opening portion at a tip of the tip portion. The control unit may cause the storage means to store the position information in response to the predetermined trigger during a step of aspirating and collecting the cell of the subject from the opening portion.

An operation method of a photoacoustic image generation apparatus according to an embodiment of the invention comprises a photoacoustic image generation unit and a control unit. The photoacoustic image generation unit generates a photoacoustic image based on a detection signal acquired by detecting a photoacoustic wave emitted from a tip portion of an insert inserted into a subject using acoustic wave detection means. The control unit responds to a predetermined trigger to cause storage means to store position information of the tip portion of the insert on the photoacoustic image for each trigger during a step of collecting a cell of the subject at the tip portion of the insert in cytology.

With the photoacoustic image generation apparatus and the operation method of the photoacoustic image generation apparatus according to the embodiment of the invention, a photoacoustic image generation unit generates a photoacoustic image based on a detection signal acquired by detecting a photoacoustic wave emitted from a tip portion of an insert inserted into a subject using acoustic wave detection means, and a control unit responds to a predetermined trigger to cause storage means to store position information of the tip portion of the insert on the photoacoustic image for each trigger during a step of collecting a cell of the subject at the tip portion of the insert in cytology. Therefore, it is possible to accurately grasp the position of the tip portion of the insert on the photoacoustic image during puncture by displaying the position information stored for each trigger on the image display unit after the examination. That is, it is possible to accurately grasp where the insert punctures in the subject after the examination. Therefore, it can be used as evidence whether or not the puncture is appropriately performed.

BRIEF DESCRIPTION OF THE DRAWINGS

FIG. 7 is a diagram for describing a movement of a syringe.

FIG. 28 is a view of an example of the two-screen display and thumbnail images on the image display unit (part 6).

DESCRIPTION OF THE PREFERRED EMBODIMENTS

Figure 1:
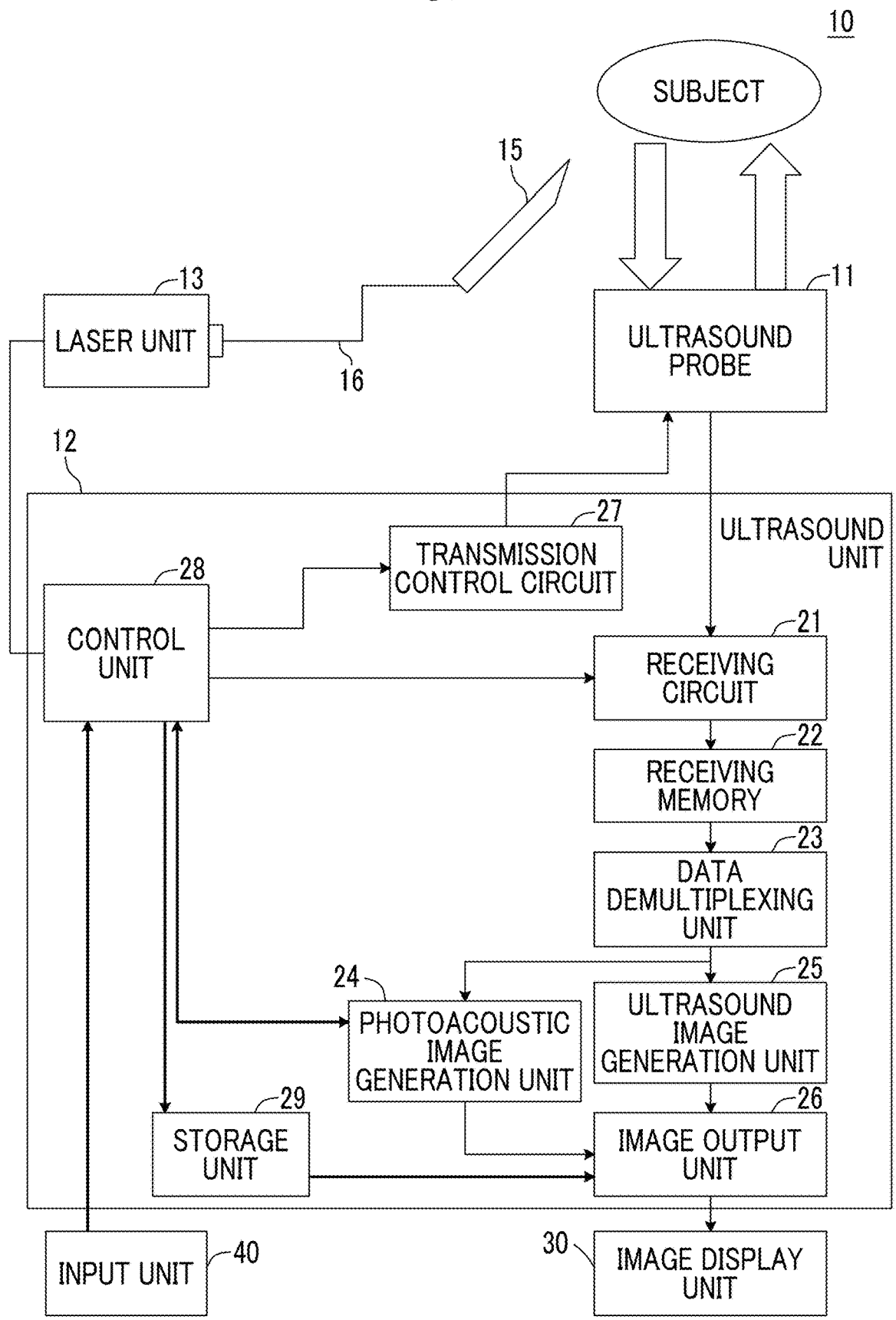
FIG. 1 is a block diagram showing a schematic configuration of a photoacoustic image generation system according to a first embodiment including a photoacoustic image generation apparatus according to an embodiment of the invention.
Figure 2:
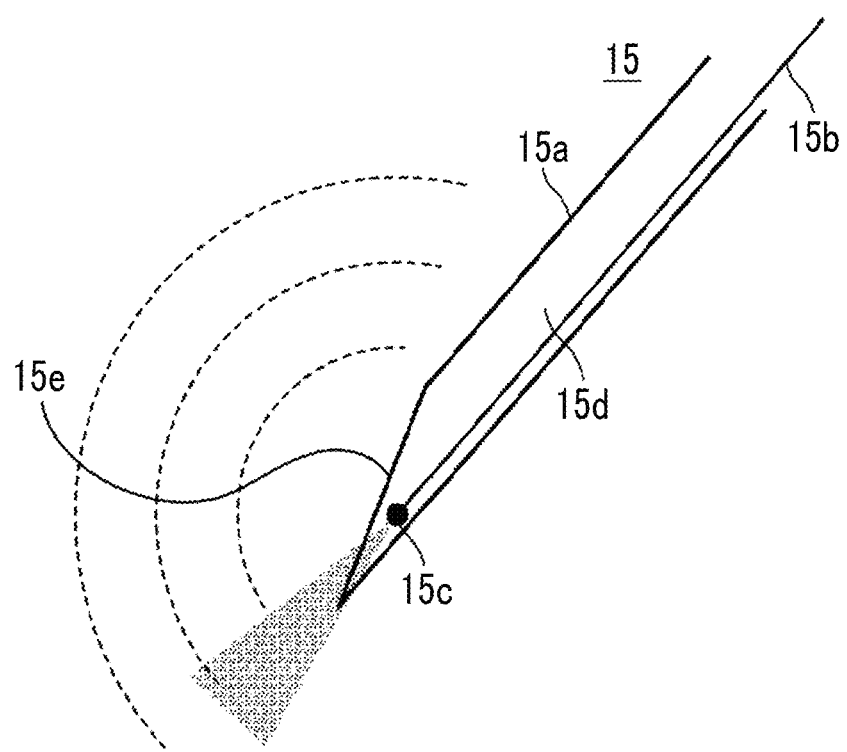
FIG. 2 is a cross-sectional view of a configuration of a tip portion of a puncture needle.

Hereinafter, a first embodiment of a photoacoustic image generation apparatus according to an embodiment of the invention will be described in detail with reference to drawings. FIG. 1 is a diagram showing a schematic configuration of a photoacoustic image generation system 10 comprising an ultrasound unit 12 corresponding to a photoacoustic image generation apparatus according to the embodiment, and FIG. 2 is a cross-sectional view of a configuration of a tip portion of a puncture needle 15.

As illustrated in FIG. 1, a photoacoustic image generation system 10 according to the embodiment comprises an ultrasound probe (probe) 11, an ultrasound unit 12, a laser unit 13, and a puncture needle 15. The puncture needle 15 and the laser unit 13 are connected by an optical cable 16 having an optical fiber. The puncture needle 15 can be attached to and detached from the optical cable 16 and is disposable. An ultrasonic wave is used as an acoustic wave in the embodiment, but the invention is not limited to the ultrasonic wave. An acoustic wave with an audible frequency may be used as long as an appropriate frequency is selected according to, for example, an inspection target or a measurement condition. Although not shown in FIG. 1, the puncture needle 15 is connected to a syringe, an infusion tube, or the like and can be used for injecting a liquid medicine. In the embodiment, a syringe S is connected to the puncture needle 15 through a tube Sb (refer to FIG. 7). The syringe S comprises a movable plunger inside, and an operation portion Sa for pushing and pulling the plunger is provided at a rear end of the plunger.

The laser unit 13 comprises a solid-state laser light source using, for example, yttrium aluminum garnet (YAG) and alexandrite. Laser light emitted from the solid-state laser light source of the laser unit 13 is guided by the optical cable 16 and is incident on the puncture needle 15. The laser unit 13 according to the embodiment emits pulsed laser light in a near-infrared wavelength range. The near-infrared wavelength range means a wavelength range of approximately 700 nm to 2500 nm. A laser diode light source is used in the embodiment. However, another laser light source such as the solid-state laser light source, a fiber laser light source, or a gas laser light source may be used or a light emitting diode light source other than the laser light source may be used.

The puncture needle 15 is an embodiment of the insert according to the embodiment of the invention and is a needle of which at least a part is punctured into a subject. FIG. 2 is a cross-sectional view including a center axis that extends in a length direction of the puncture needle 15. The puncture needle 15 includes a puncture needle main body 15a that has a tip opening 15e at an acute tip and is formed in a hollow shape, an optical fiber 15b that guides laser light emitted from the laser unit 13 to the vicinity of the tip opening 15e of the puncture needle 15, and a photoacoustic wave generation portion 15c that absorbs laser light emitted from the optical fiber 15b and generates a photoacoustic wave.

The optical fiber 15b and the photoacoustic wave generation portion 15c are disposed in a hollow portion 15d of the puncture needle main body 15a. For example, the optical fiber 15b is connected to the optical fiber in the optical cable 16 (refer to FIG. 1) through an optical connector that is provided at a base end of the puncture needle 15. For example, laser light of 0.2 mJ is emitted from a light emission end of the optical fiber 15b.

The photoacoustic wave generation portion 15c is provided at the light emission end of the optical fiber 15b and is provided near the tip of the puncture needle 15 and in the inner wall of the puncture needle main body 15a. The photoacoustic wave generation portion 15c absorbs the laser light emitted from the optical fiber 15b and generates photoacoustic waves. The photoacoustic wave generation portion 15c is made of, for example, an epoxy resin, a polyurethane resin, a fluorine resin, and silicone rubber with which a black pigment is mixed. The photoacoustic wave generation portion 15c is illustrated to be larger than the optical fiber 15b in FIG. 2, but the invention is not limited thereto. The photoacoustic wave generation portion 15c may have a size that is equal to a diameter of the optical fiber 15b.

The photoacoustic wave generation portion 15c is not limited to the above, and a metal film or an oxide film having light absorptivity with respect to the wavelength of laser light may be used as the photoacoustic wave generation portion. An oxide film made of, for example, iron oxide, chromium oxide, or manganese oxide having high light absorptivity with respect to the wavelength of laser light can be used as the photoacoustic wave generation portion 15c. Alternatively, a metal film made of, for example, titanium (Ti) or platinum (Pt) that has lower light absorptivity than an oxide but higher biocompatibility than an oxide may be used as the photoacoustic wave generation portion 15c. In addition, a position where the photoacoustic wave generation portion 15c is provided is not limited to the inner wall of the puncture needle main body 15a. For example, a metal film or an oxide film which is the photoacoustic wave generation portion 15c may be formed on the light emission end of the optical fiber 15b with a film thickness of about 100 nm by vapor deposition such that the oxide film covers the light emission end. In this case, at least a part of the laser light emitted from the light emission end of the optical fiber 15b is absorbed by the metal film or the oxide film covering the light emission end and the photoacoustic wave is generated from the metal film or the oxide film.

The "near the tip of the puncture needle 15" means a position where a photoacoustic wave with which a position of the tip of the puncture needle 15 can be captured with accuracy required for the puncture work can be generated in a case where the tip of the optical fiber 15b and the photoacoustic wave generation portion 15c are disposed at the position. For example, the "near the tip thereof" refers to a range of 0 mm to 3 mm from the tip of the puncture needle 15 to a base end side. In the following embodiments, the "near the tip thereof" has the same meaning. In the embodiment, the puncture needle 15 is used in a case where the FNA is performed. In the embodiment, the FNA is performed in a case where there is a suspicion of a lesion (breast cancer) in image diagnosis such as mammography or an ultrasonic wave. In the FNA, a cell that exists in a target region T is collected by the puncture needle 15 with a region having a suspicion of breast cancer in a breast as the target region T. In general, a diameter of the needle used for histology is often 1.4 mm to 4 mm, whereas a diameter of the needle used for cytology is about 0.4 to 2 mm. However, the size of the puncture needle 15 is not limited thereto and can be changed as appropriate depending on a target from which a cell is collected. In the embodiment, the cell in the breast is collected in the FNA. However, the invention is not limited thereto and may be adapted to a case of collecting a cell of a lesion portion, such as thyroid gland, or lymph node, that cannot be touched with a brush or a cotton swab, that is, to which scratch cytology cannot be adapted.

Returning to FIG. 1, the ultrasound probe 11 corresponds to acoustic wave detection means according to the embodiment of the invention and has, for example, a plurality of detector elements (ultrasound vibrators) arranged one-dimensionally. Returning to FIG. 1, the ultrasound probe 11 detects the photoacoustic wave emitted from the photoacoustic wave generation portion 15c after the puncture needle 15 is punctured into the subject. The ultrasound probe 11 transmits the acoustic wave (ultrasonic wave) to the subject and receives the reflected acoustic wave (reflected ultrasonic wave) with respect to the transmitted ultrasonic wave, in addition to the detection of the photoacoustic wave. The transmission and reception of the ultrasonic wave may be performed at separated positions. For example, the ultrasonic wave may be transmitted from a position different from the ultrasound probe 11, and the ultrasound probe 11 may receive the reflected ultrasonic wave with respect to the transmitted ultrasonic wave. It is possible to use a linear ultrasound probe, a convex ultrasound probe, a sector ultrasound probe, or the like as the ultrasound probe 11. A two-dimensional array may be used.

The ultrasound unit 12 includes a receiving circuit 21, a receiving memory 22, a data demultiplexing unit 23, a photoacoustic image generation unit 24, an ultrasound image generation unit 25, an image output unit 26, a transmission control circuit 27, a control unit 28, and a storage unit 29 (an example of storage means in the invention). The ultrasound unit 12 typically has, for example, a processor, a memory, and a bus. In the ultrasound unit 12, a program relating to photoacoustic image generation processing, ultrasound image generation processing, and the like is incorporated in a memory. The program is operated by the control unit 28 which is composed of the processor to realize functions of the data demultiplexing unit 23, the photoacoustic image generation unit 24, the ultrasound image generation unit 25, the image output unit 26. That is, each of these units is composed of the memory into which the program is incorporated and the processor.

In the embodiment, the processor executes the program to function each unit. However, the invention is not limited thereto, and a part or all of the functions may be realized by hardware. The hardware configuration is not particularly limited and can be formed by combining a plurality of integrated circuits (ICs), an application specific integrated circuit (ASIC), a field-programmable gate array (FPGA), and a circuit including a memory and a discrete component as appropriate.

The receiving circuit 21 receives a detection signal output from the ultrasound probe 11 and stores the received detection signal in the receiving memory 22. The receiving circuit 21 typically includes a low-noise amplifier, a variable-gain amplifier, a low pass filter, and an analog to digital convertor (AD convertor). The detection signal of the ultrasound probe 11 is amplified by the low-noise amplifier, is subjected to gain adjustment corresponding to a depth by the variable-gain amplifier, is converted into a digital signal by the AD converter after high-frequency components of the detection signal is cut by the low pass filter, and then is stored in the receiving memory 22. The receiving circuit 21 is composed of, for example, one integrated circuit (IC).

The ultrasound probe 11 outputs a detection signal of the photoacoustic wave and a detection signal of the reflected ultrasonic wave. The receiving memory 22 stores the AD-converted detection signals (sampling data) of the photoacoustic wave and the reflected ultrasonic wave. The data demultiplexing unit 23 reads out the sampling data of the detection signal of the photoacoustic wave from the receiving memory 22 and transmits the detection signal to the photoacoustic image generation unit 24. The data demultiplexing unit 23 reads out the sampling data of the detection signal of the reflected ultrasonic wave from the receiving memory 22 and transmits the detection signal to the ultrasound image generation unit 25.

The photoacoustic image generation unit 24 generates a photoacoustic image based on the detection signal of the photoacoustic wave detected by the ultrasound probe 11. The photoacoustic image generation includes, for example, image reconfiguration such as phase matching addition, detection, and logarithmic conversion. A portion of the photoacoustic wave generation portion 15c appears as a bright point in the photoacoustic image. Therefore, it is possible to check a position of the puncture needle 15 using the photoacoustic image. The ultrasound image generation unit 25 generates an ultrasound image (reflected acoustic wave image) based on the detection signal of the reflected ultrasonic wave detected by the ultrasound probe 11. The ultrasound image generation also includes image reconfiguration such as phase matching addition, detection, logarithmic conversion, and the like. The image output unit 26 outputs at least one of the photoacoustic image or the ultrasound image to an image display unit 30 such as a display apparatus. The image output unit 26 outputs photoacoustic image data stored in the storage unit 29 described below to the image display unit 30.

The control unit 28 controls each unit in the ultrasound unit 12. In a case where a photoacoustic image is acquired, the control unit 28 transmits a trigger signal to the laser unit 13 to cause the laser unit 13 to emit laser light. In addition, the control unit 28 transmits a sampling trigger signal to the receiving circuit 21 to control a sampling start timing of the photoacoustic wave or the like with the emission of the laser light.

In a case where an ultrasound image is acquired, the control unit 28 transmits an ultrasound transmission trigger signal for instructing the transmission control circuit 27 to transmit the ultrasonic wave. In a case where the ultrasound transmission trigger signal is received, the transmission control circuit 27 causes the ultrasound probe 11 to transmit the ultrasonic wave. The ultrasound probe 11 detects a reflected ultrasonic wave by scanning while shifting acoustic lines line by line, for example. The control unit 28 transmits the sampling trigger signal to the receiving circuit 21 according to a transmission timing of the ultrasonic wave to start the sampling of the reflected ultrasonic wave.

In addition, the control unit 28 according to the embodiment responds to a predetermined trigger during a step of collecting the subject cell at the tip portion of the puncture needle 15 in the FNA to store position information of the tip portion of the puncture needle 15 on the photoacoustic image for each trigger in the storage unit 29 described below. In the embodiment, the control unit 28 stores a still image of a real-time photoacoustic image generated by the photoacoustic image generation unit 24 in the storage unit 29 as the position information of the tip portion of the puncture needle 15 on the photoacoustic image. The control unit 28 comprises a needle tip visualization (NTV) mode for turning on or off the display of the photoacoustic image generated by the photoacoustic image generation unit 24 on the image display unit 30. The control unit 28 causes the image display unit 30 to display the photoacoustic image in a case where an NTV mode is turned on by an input unit 40 described below. The photoacoustic image is displayed on the ultrasound image displayed on the image display unit 30 in an overlaid manner.

The storage unit 29 stores the position information of the tip portion of the puncture needle 15 on the photoacoustic image and outputs the position information or the like stored in response to an instruction from the control unit 28 to the image output unit 26. In the embodiment, the above still image of the photoacoustic image is stored.

More specifically, the image display unit 30 is an image display screen including, for example, a liquid crystal display device. The image display unit 30 may be composed of a touch panel that can be directly input by an operator. The image display unit 30 may display the photoacoustic wave image and the ultrasound image separately or combinedly. It is possible to check where the tip of the puncture needle 15 is in the living body with the combined display of the photoacoustic wave image and the ultrasound image. Therefore, an accurate and safe puncture is possible.

The input unit 40 is composed of a mouse, a keyboard, or the like and comprises, for example, a touch panel different from the image display unit 30, a plurality of input buttons including a save button and an NTV Overlay button, a plurality of input keys, and the like (not shown). The save button is a button for inputting the trigger signal to the control unit 28, and the NTV Overlay button is a button for overlaying and displaying all overlaid images I described below stored in the storage unit 29 on an ultrasound image Ib displayed on the image display unit 30 (not shown).

Figure 3:
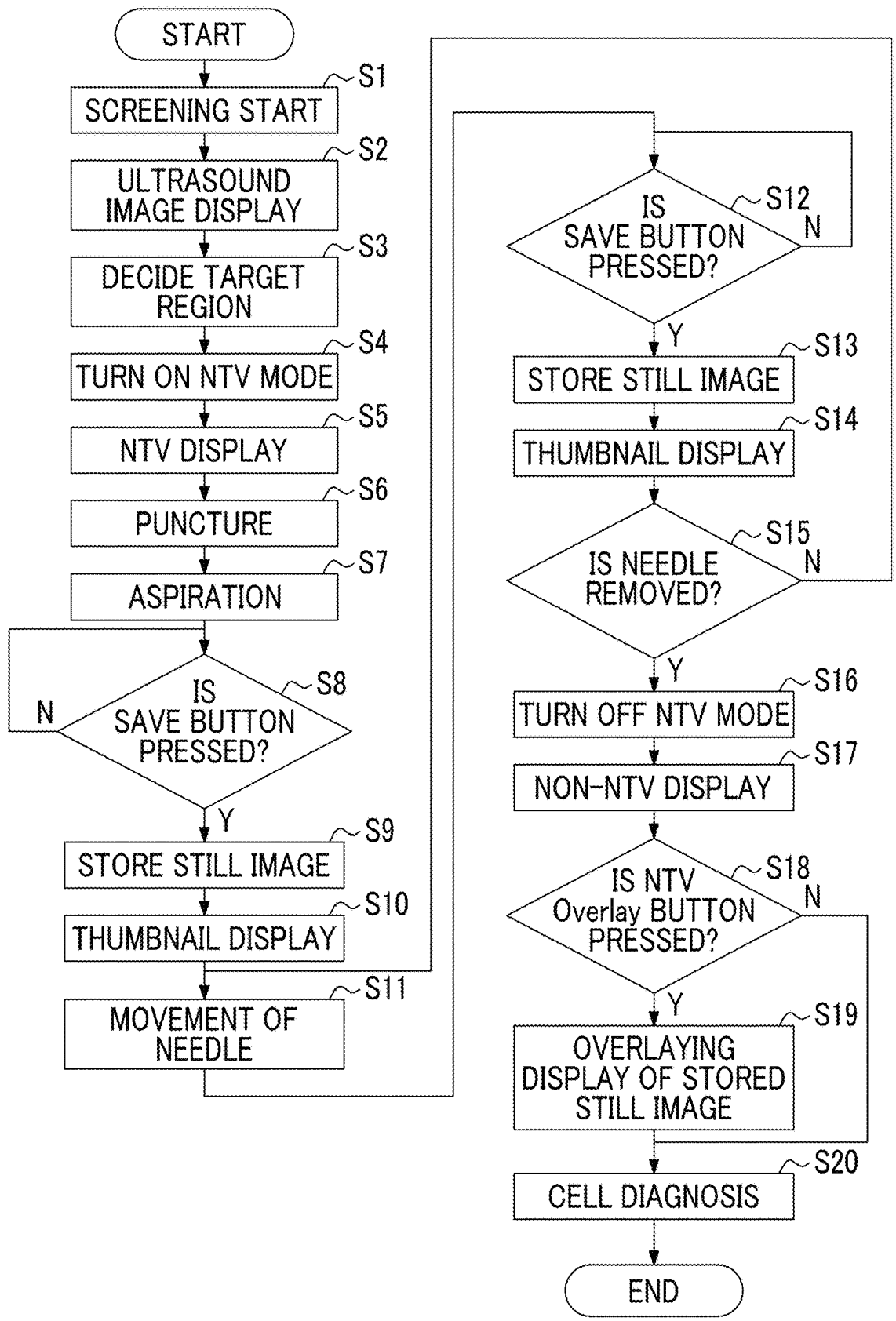
FIG. 3 is a flowchart of a series of pieces of processing of FNA including an operation method the photoacoustic image generation system.
Figure 4:
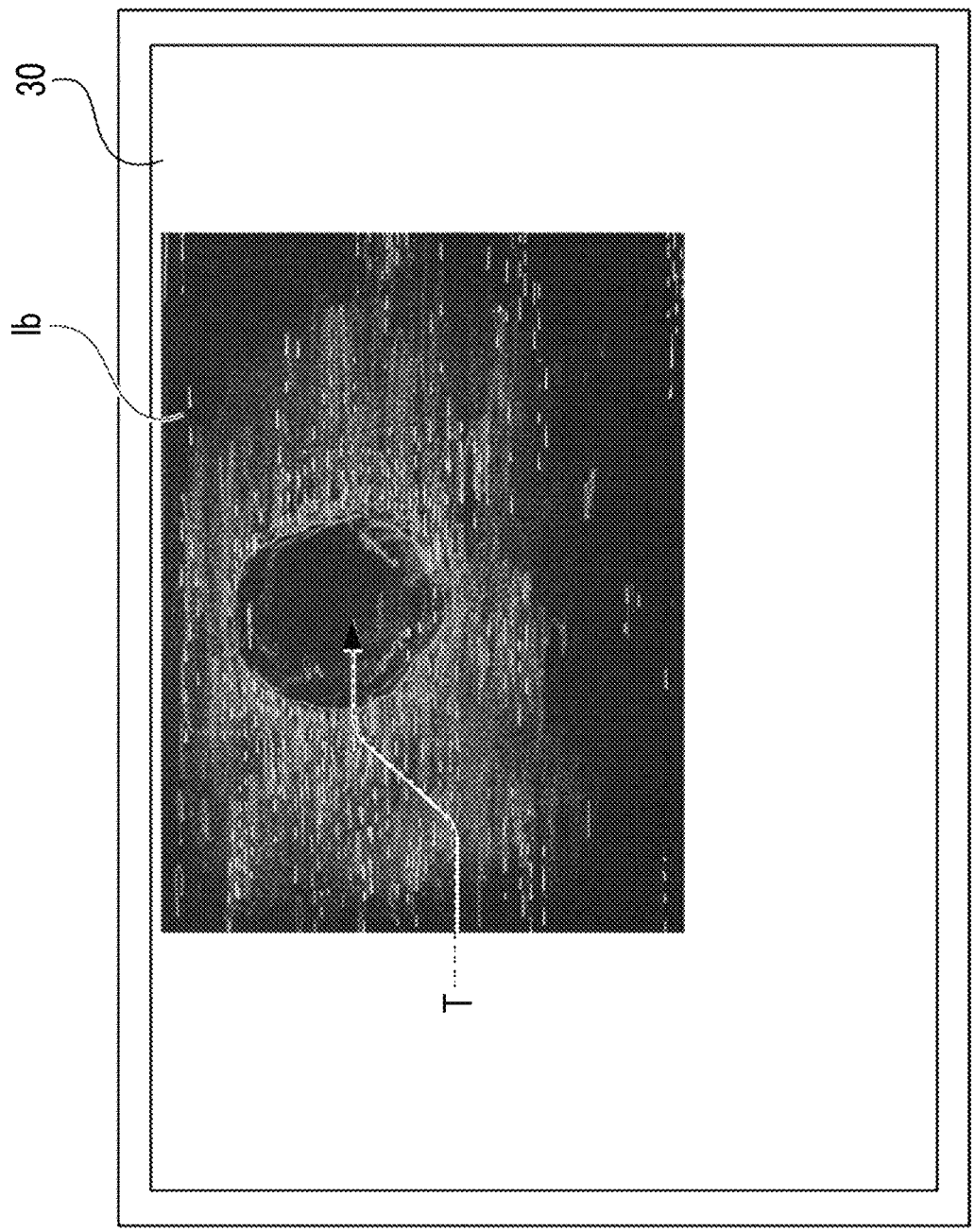
FIG. 4 is a view of an example of an ultrasound image displayed on an image display unit.
Figure 5:
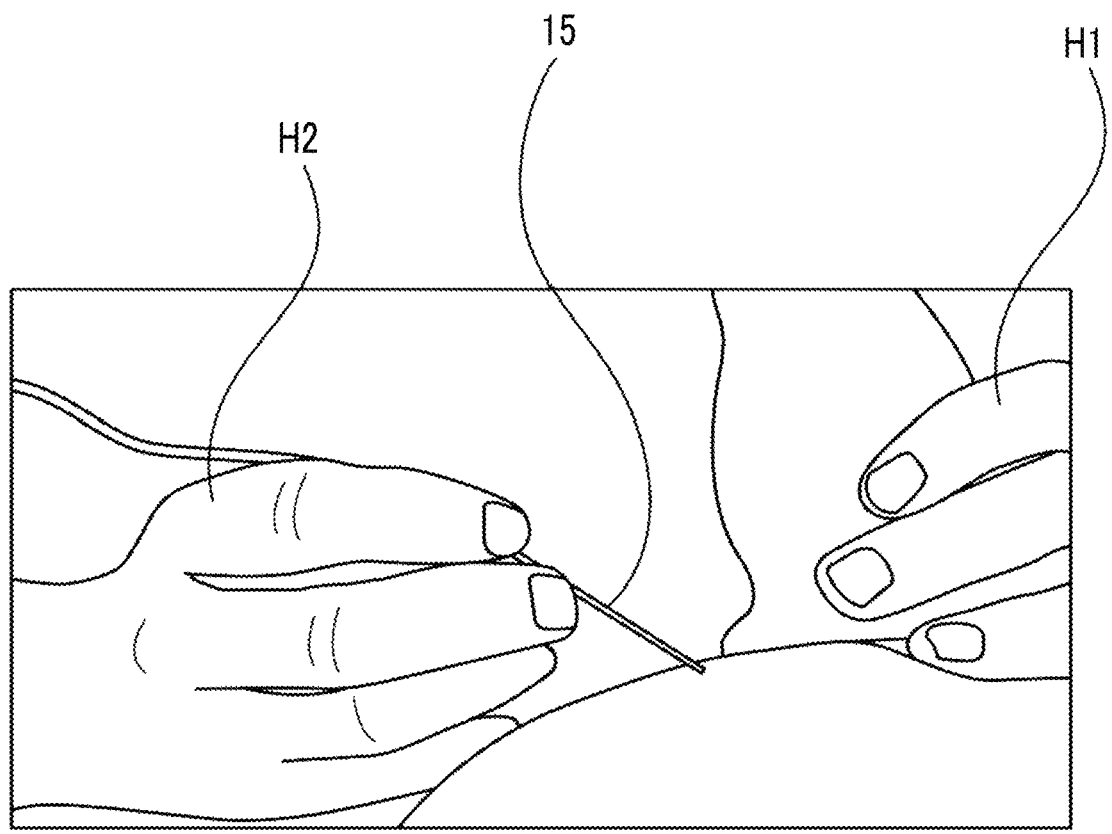
FIG. 5 is a diagram showing an example of an operation method of an ultrasound probe and a puncture needle.
Figure 6:
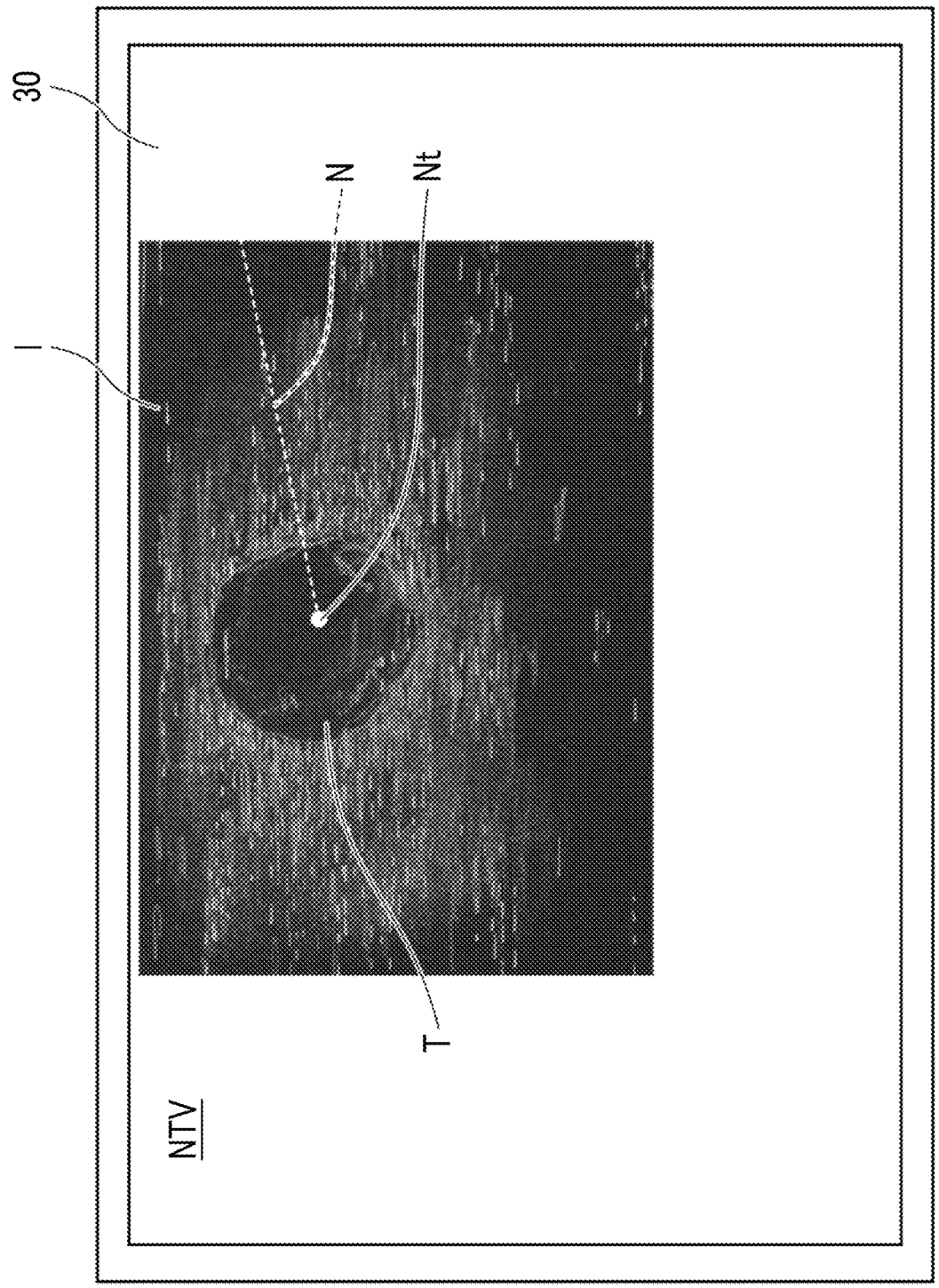
FIG. 6 is a view of an example of an NTV display displayed on the image display unit.
Figure 11:
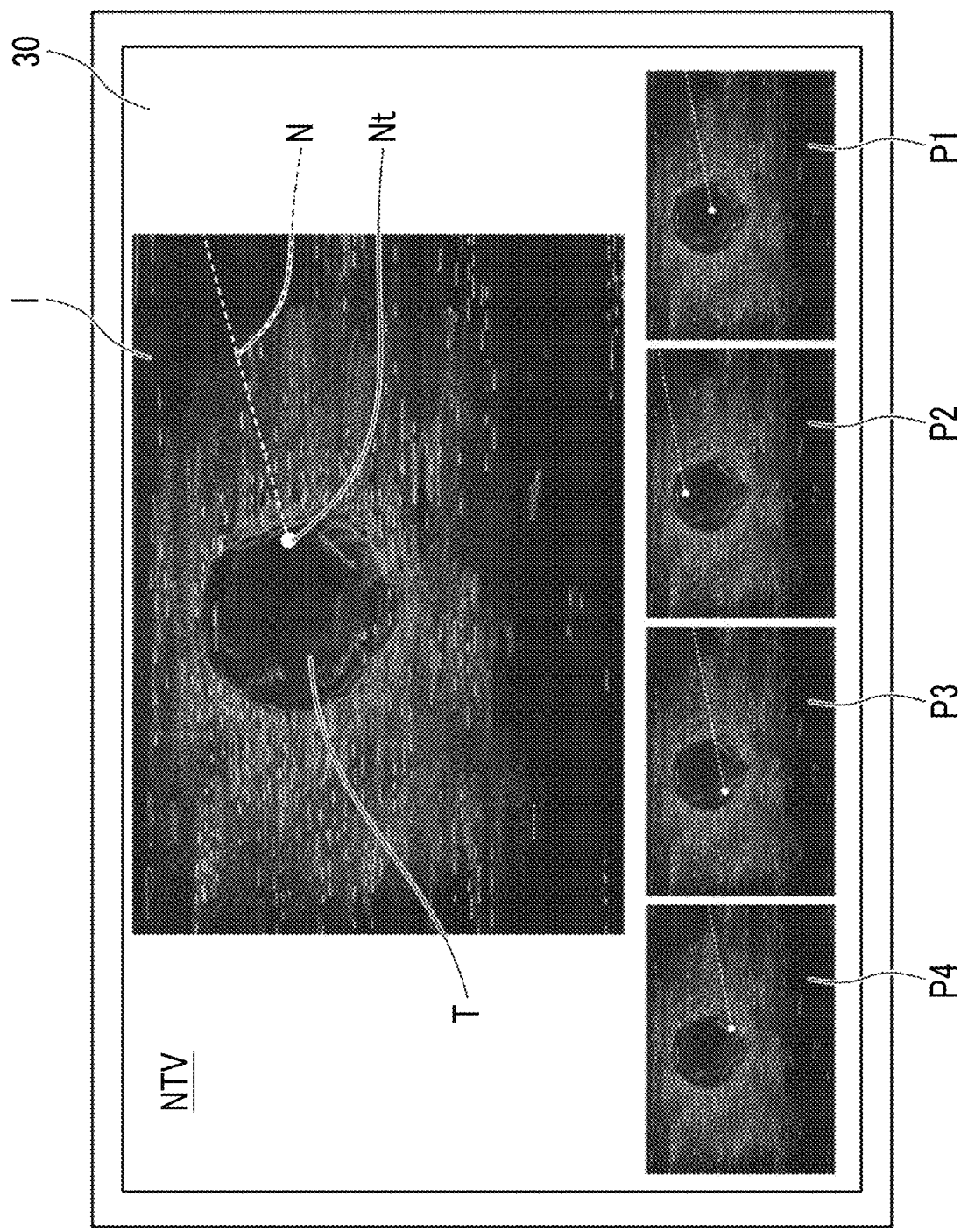
FIG. 11 is a view of an example of an NTV display and a thumbnail image displayed on the image display unit (part 4).
Figure 12:
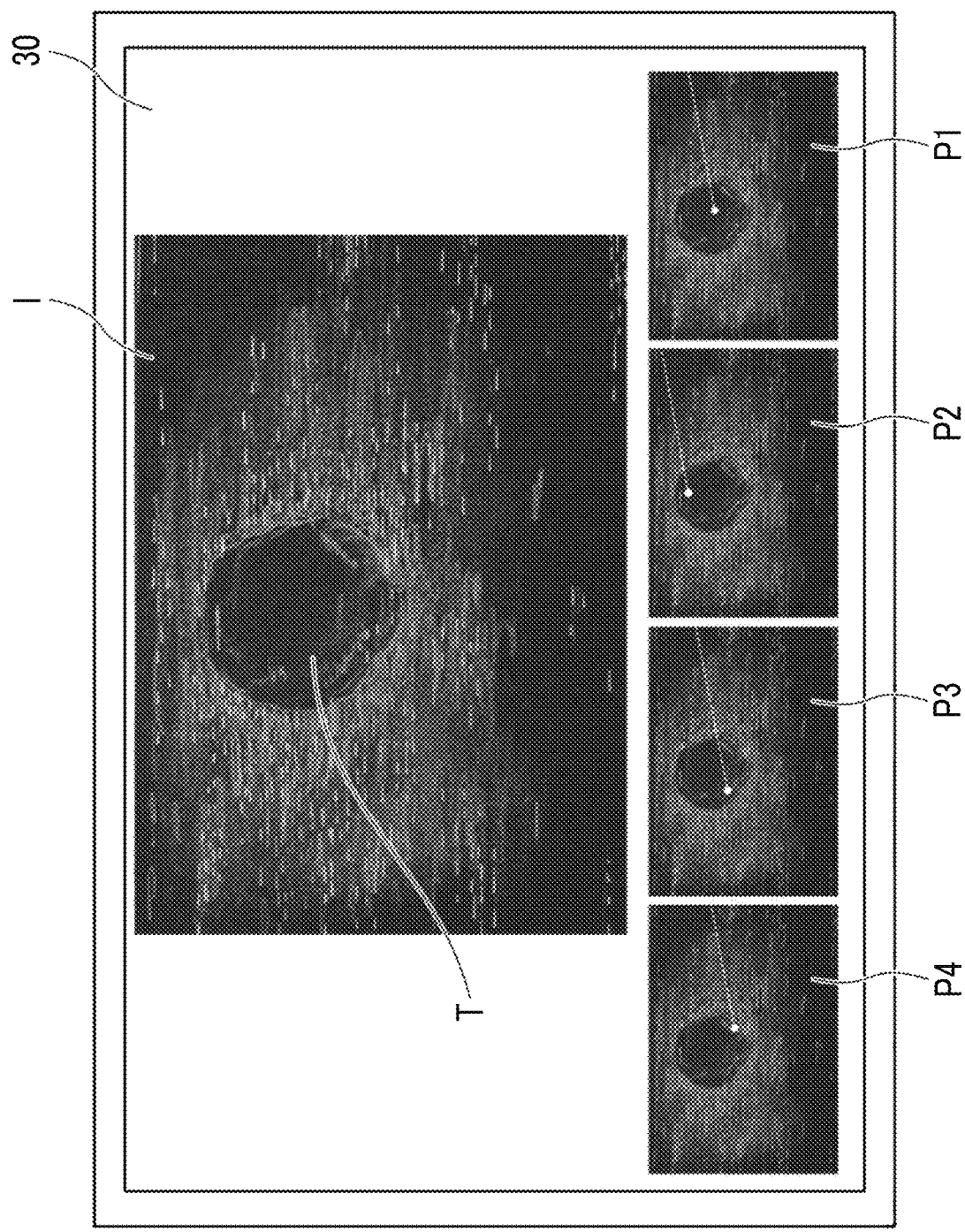
FIG. 12 is a view of an example of an ultrasound image and thumbnail images displayed on the image display unit.
Figure 13:
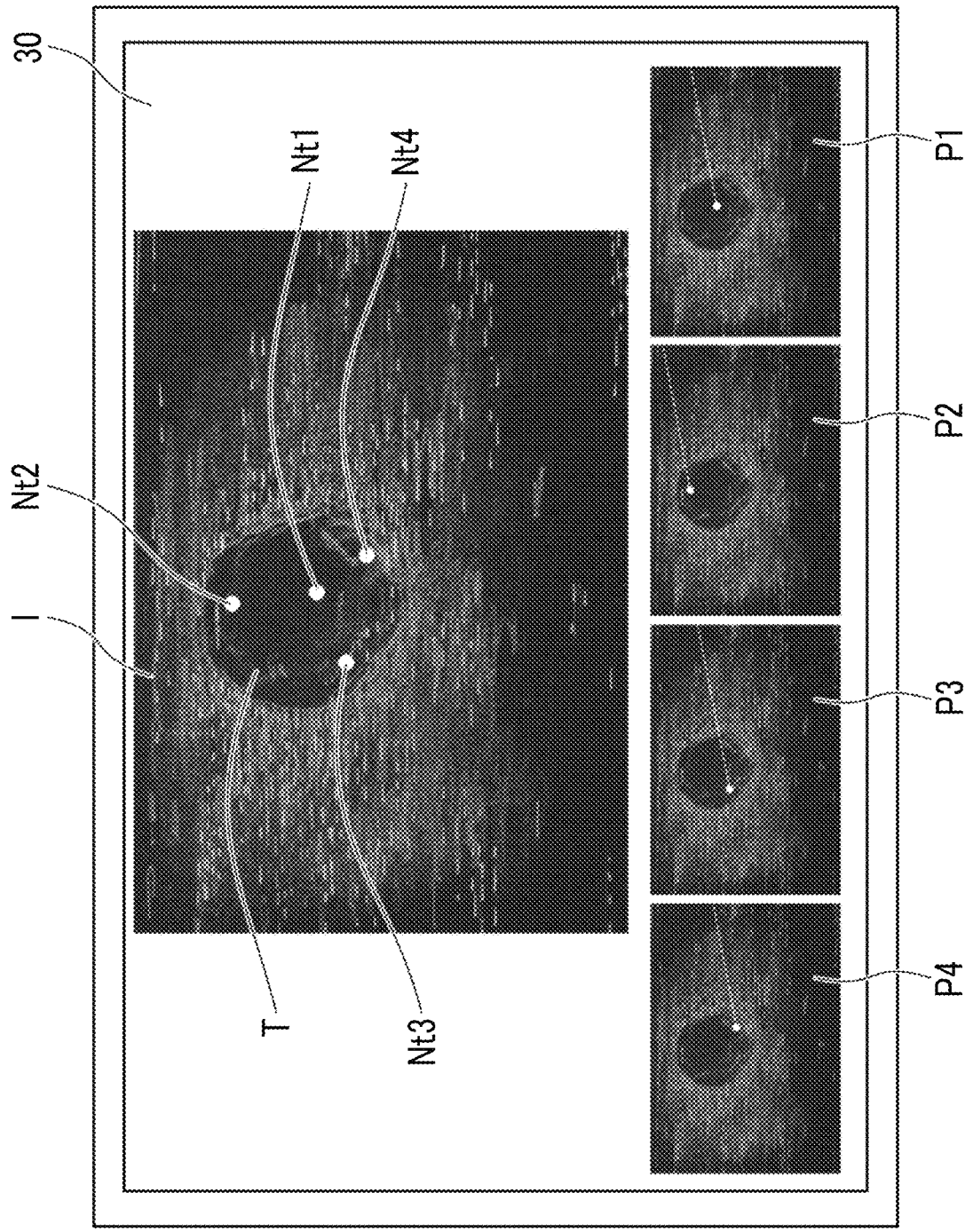
FIG. 13 is a view of an example of an NTV Overlay image and thumbnail images displayed on the image display unit (part 1).
Figure 14:
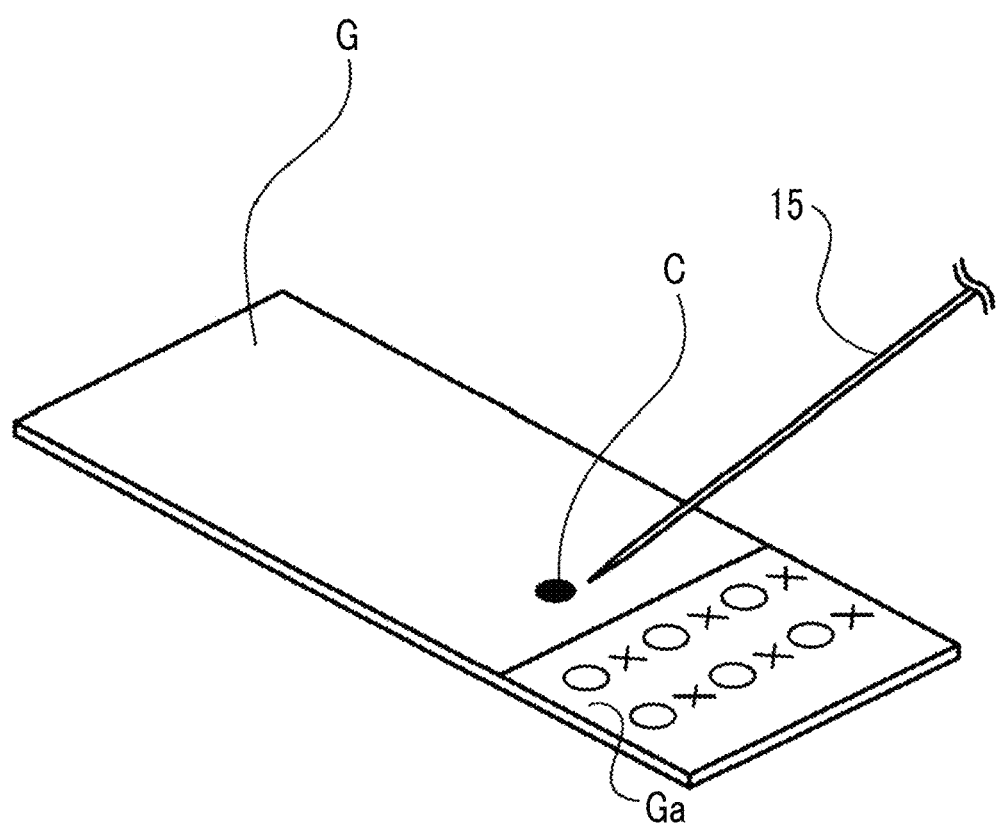
FIG. 14 is a diagram showing an example of a preparation.

Next, a series of pieces of processing of the FNA including the operation method of the photoacoustic image generation system 10 comprising the ultrasound unit 12 according to the embodiment will be described with reference to a flowchart shown in FIG. 3. FIG. 3 is the flowchart of the series of pieces of processing of the FNA including the operation method of the photoacoustic image generation system 10, FIG. 4 is a view of an example of the ultrasound image Ib displayed on the image display unit 30, FIG. 5 is a diagram showing an example of an operation method of an ultrasound probe 11 and a puncture needle 15, FIG. 6 is a view of an example of an NTV display displayed on the image display unit 30, FIG. 7 is a diagram for describing a movement of a syringe S, FIGS. 8 to 11 are views of examples of an NTV display and a thumbnail image displayed on the image display unit 30, respectively, FIG. 12 is a view of an example of an ultrasound image Ib and thumbnail images displayed on the image display unit 30, FIG. 13 is a view of an example of an NTV Overlay image Io and thumbnail images displayed on the image display unit 30, and FIG. 14 is a diagram showing an example of a preparation. In the embodiment, the FNA performed in the case where there is a suspicion of a lesion (breast cancer) in image diagnosis such as mammography or ultrasonic wave will be described below as an example. Specifically, the cell that exists in the target region T is collected by the puncture needle 15 with the region having the suspicion of breast cancer in the breast as the target region T.

As shown in FIG. 3, the ultrasound probe 11 is first scanned on a breast of a subject by a user such as a doctor and screening is started (step S1). In a case where a signal is received from the ultrasound probe 11, the ultrasound unit 12 causes the image display unit 30 to display the ultrasound image Ib as shown in FIG. 4 (step S2). As shown in FIG. 5, for example, the user decides the region having the suspicion of breast cancer in the breast, that is, the target region T while operating the ultrasound probe 11 with the left hand H1, operating the puncture needle 15 with the right hand H2, and checking the displayed ultrasound image Ib (step S3).

In a case where the target region T is decided, the user operates the input unit 40 to turn on the NTV mode (step S4), and the control unit 28 causes the image display unit 30 to display a photoacoustic image generated by the photoacoustic image generation unit 24 through the image output unit 26 as shown in FIG. 6. The image output unit 26 overlays and displays the ultrasound image Ib and the photoacoustic image on the image display unit 30, and performs the NTV display on the image display unit 30 (step S5). Here, in the embodiment, an image obtained by overlaying and combining the ultrasound image Ib and the photoacoustic image is referred to as the overlaid image I. The display of the photoacoustic image on the image display unit 30 is referred to as the NTV display. In the embodiment, the NTV display causes the image display unit 30 to display the overlaid image I obtained by overlaying and combining the real-time photoacoustic image generated by the photoacoustic image generation unit 24 and the real-time ultrasound image Ib generated by the ultrasound image generation unit 25.

Further, the control unit 28 causes the image display unit 30 to display, for example, a character of NTV through the image output unit 26 such that it can be visually recognized that the image display unit 30 is in the NTV display, that is, the NTV mode is turned on. The character to be displayed is not limited to the NTV. For example, an icon-based graphical user interface (GUI) may be used as long as it can be visually recognized that the display is the NTV display. A color of the NTV character is not particularly limited and can be randomly changed by the operator. In the photoacoustic image, the position of the tip of the puncture needle 15 in the image may be detected, and the detected tip of the puncture needle 15 may be displayed in a highlighted manner on the image display unit 30. In a case of highlighting, for example, a position of a maximum brightness point in the photoacoustic image may be detected as the position of the tip portion of the puncture needle 15, as a method of detecting the position of the tip portion of the puncture needle 15.

In a case where the image display unit 30 is in the NTV display (step S5), the user punctures the subject with the puncture needle 15 at any timing such as before and after the laser unit 13 is driven (step S6), and the puncture needle 15 is inserted into the subject. In a case where the puncture needle 15 is inserted into the subject, the tip portion of the puncture needle 15 inserted into the subject appears as the brightest bright point on the overlaid image I as shown in FIG. 6. In the embodiment, hereinafter, the puncture needle 15 to be displayed on the overlaid image I is referred to as a puncture needle N, and a tip portion of the puncture needle N is referred to as a tip portion Nt. The tip portion Nt of the puncture needle N may be displayed in any color that can be selected by the operator or may be blinked. The puncture needle N may be displayed thicker than an actual needle, that is, in a highlighted manner for easy viewing, or may be adjusted as appropriate on an apparatus side. The puncture needle N may not be displayed on the overlaid image I in a case where the needle cannot be recognized on the overlaid image I. The tip portion Nt may also be displayed in a more highlighted manner than an actual bright point. It is possible for the user to randomly set the display methods of the puncture needle N and the tip portion Nt.

In a case where the tip portion Nt of the puncture needle N reaches the target region T on the overlaid image I, a syringe operator H pulls the operation portion Sa toward the syringe operator H side, that is, forward to aspirate a cell inside the target region T from the tip opening 15e of the puncture needle 15 through the tube Sb as shown in FIG. 7 (step S7). The syringe operator H who operates the syringe S is a person different from the user who operates the ultrasound probe 11 and the puncture needle 15. The control unit 28 determines whether or not the trigger signal is input from the input unit 40 to determine whether or not the save button is pressed during the cell aspiration (step S8). In a case where the control unit 28 determines that the save button is not pressed (step S8; N), the processing of step S8 is repeated until the save button is pressed. On the other hand, in a case where the control unit 28 determines that the save button is pressed (step S8; Y), the control unit 28 stores the still image of the overlaid image I in the storage unit 29 (step S9). In the case, the photoacoustic image constituting the overlaid image I is also stored in the storage unit 29 as position information of the tip portion Nt of the puncture needle N. The ultrasound image constituting the overlaid image I is also stored in the storage unit 29. The save button may be pressed by the user, may be pushed by the syringe operator H, or may be pushed by another person, and the invention is not particularly limited thereto.

It is possible to acquire the position information at any timing of the user by storing position information of the tip portion Nt of the puncture needle N at a timing when the save button is pressed while the cell inside the target region T is being aspirated from the tip opening 15e of the puncture needle 15. It is possible to acquire the position information of a position where the cell is aspirated, by pressing the save button at a timing when the user moves the puncture needle N in the target region T.

Figure 8:
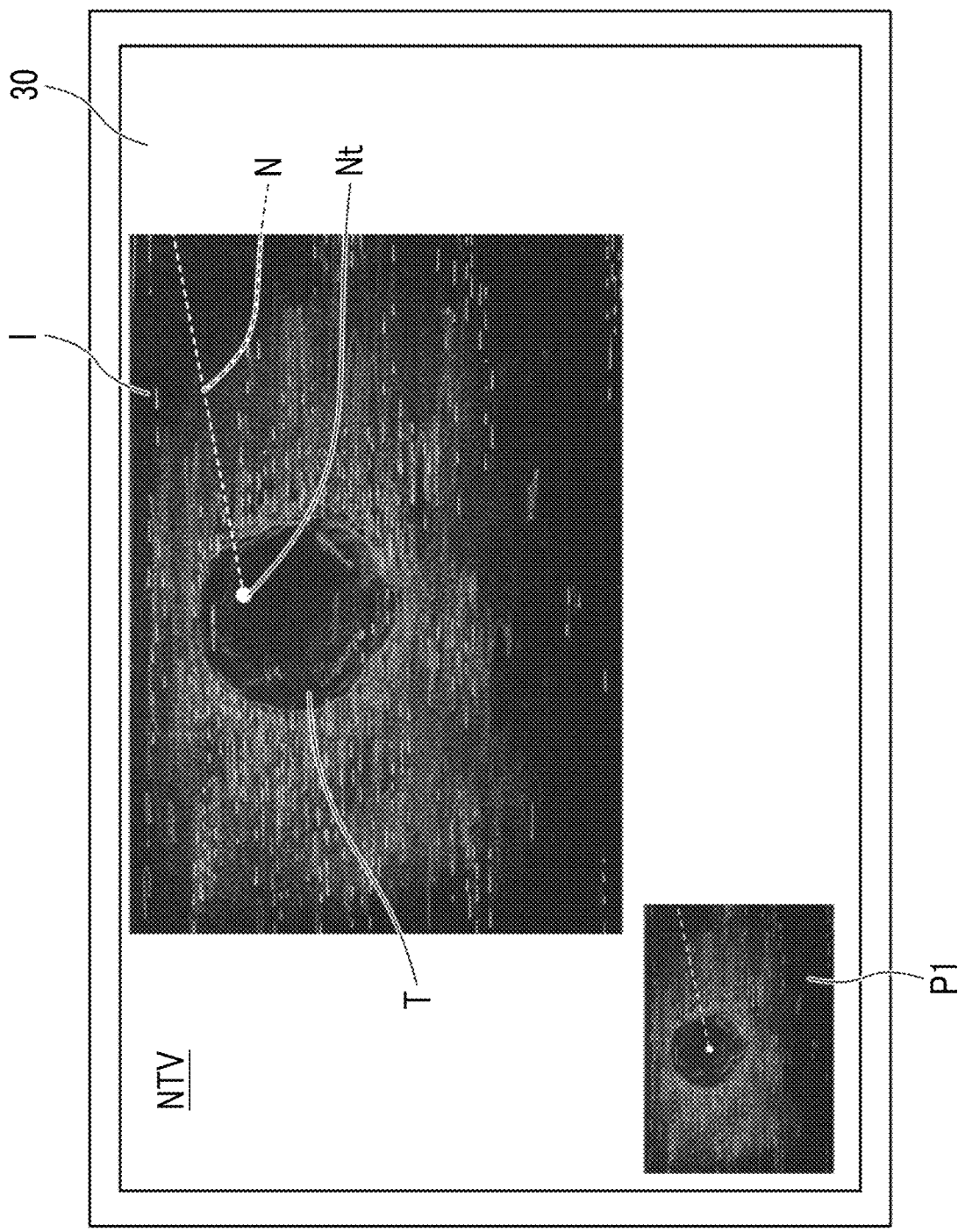
FIG. 8 is a view of an example of an NTV display and a thumbnail image displayed on the image display unit (part 1).
Figure 9:
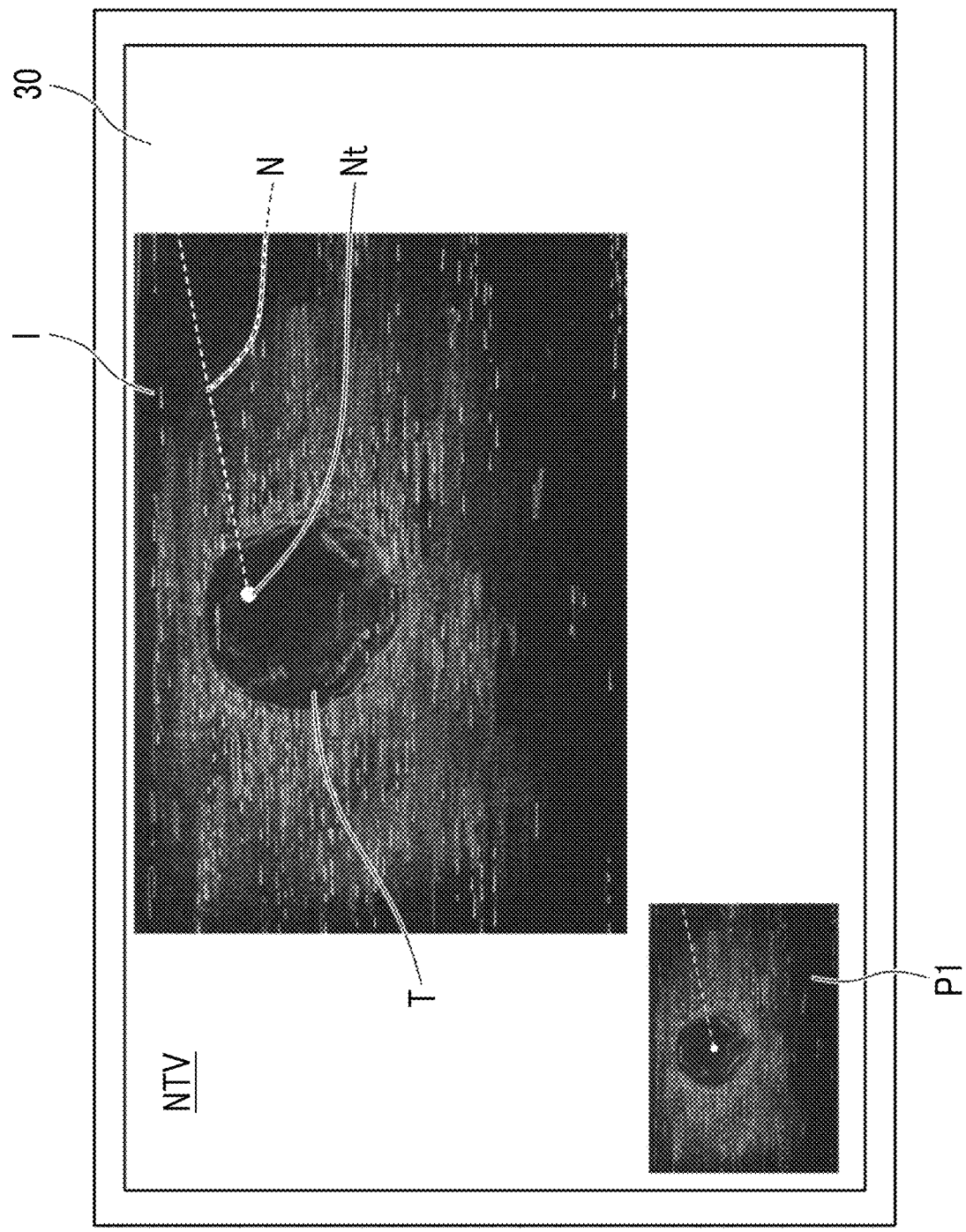
FIG. 9 is a view of an example of an NTV display and a thumbnail image displayed on the image display unit (part 2).

As shown in FIG. 8, the control unit 28 causes the image display unit 30 to display the overlaid image I stored in the storage unit 29 as a thumbnail (step S9). In the embodiment, the control unit 28 displays a thumbnail image P1 of the overlaid image I at the lower left on the image display unit 30, that is, below the overlaid image I. Next, the puncture needle 15 is moved to another position inside the target region T by the user as shown in FIG. 9 (step S11). In the embodiment, the puncture needle 15 is moved while the aspiration is performed by the syringe S in a state where the puncture needle 15 is inserted into the subject.

The control unit 28 determines whether or not the save button is pressed (step S12). In a case where the control unit 28 determines that the save button is not pressed (step S12; N), the processing of step S12 is repeated until the save button is pressed. On the other hand, in a case where the control unit 28 determines that the save button is pressed (step S12; Y), the control unit 28 stores the still image of the overlaid image I after the movement of the puncture needle 15 in the storage unit 29 (step S13). In the case, the photoacoustic image constituting the overlaid image I after movement is also stored as the position information of the tip portion Nt of the puncture needle N.

Figure 10:
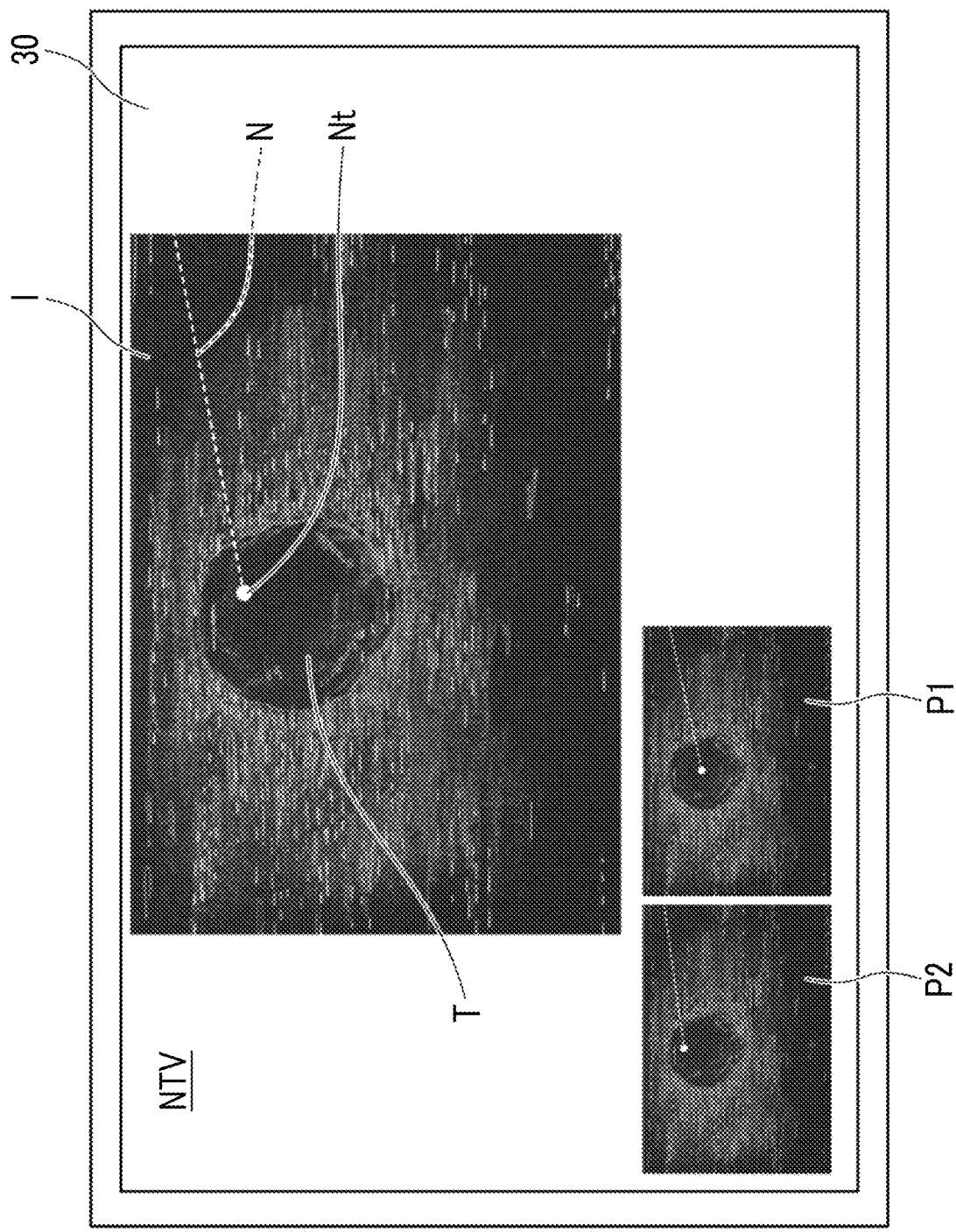
FIG. 10 is a view of an example of an NTV display and a thumbnail image displayed on the image display unit (part 3).

As shown in FIG. 10, the control unit 28 causes the image display unit 30 to display the overlaid image I after the movement stored in the storage unit 29 as a thumbnail (step S14). The control unit 28 displays a thumbnail image P2 of the overlaid image I stored this time on the left side of the thumbnail image P1 of the overlaid image I stored last time. A display order of the thumbnails can be set in advance by the user. In the embodiment, the display is performed such that the last stored thumbnail image of the overlaid image I is displayed at the left end. Next, the control unit 28 determines whether or not the puncture needle 15 is removed from the subject (step S15). In a case where the puncture needle 15 is determined to be not removed (step S15; N), the control unit 28 shifts the processing to step S11 and repeats subsequent processing. In the embodiment, the pieces of processing in steps S11 to S14 are repeated three times, and the control unit 28 displays four thumbnail images P1 to P4 as shown in FIG. 11. In the embodiment, four pieces of position information of the tip portion Nt of the puncture needle N are acquired assuming that the user collects cells at four locations in the target region T. However, the invention is not limited thereto. Five or six pieces of position information of the tip portion Nt are acquired in a case where cells are collected at five or six locations. Ten pieces of position information of the tip portion Nt are acquired in a case where cells are collected at ten locations. The locations where the cells are collected vary depending on a type, size, or the like of the target, but the position information of the tip portion Nt is acquired at all locations where the cells are collected in the invention.

On the other hand, in a case where the control unit 28 determines in step S15 that the puncture needle 15 is removed (step S15; Y), the control unit 28 turns off the NTV mode (step S16) and does not display the NTV character on the image display unit 30 through the image output unit 26 as shown in FIG. 12 (step S17). That is, the image display unit 30 displays the real time image of the ultrasound image Ib and the thumbnail images P1 to P4 of the overlaid image I stored in the storage unit 29 as shown in FIG. 12.

The control unit 28 determines whether or not the NTV Overlay button is pressed (step S18). In a case where the control unit 28 determines that the NTV Overlay button is not pressed (step S18; N), the collected cells are diagnosed as described below (step S20) and the series of pieces of processing ends. On the other hand, in a case where the control unit 28 determines that the NTV Overlay button is pressed (step S18; Y), the control unit 28 overlays and displays still images of all the photoacoustic images stored in the storage unit 29 on the ultrasound image displayed on the image display unit 30 as shown in FIG. 13 (step S19). In the embodiment, this display is referred to as an NTV Overlay display, and the displayed image is referred to as the NTV Overlay image Io. For example, an NTV Overlay character is displayed on the image display unit 30 through the image output unit 26 such that it can be visually recognized that the still images of all the photoacoustic images are overlaid and displayed. The character to be displayed is not limited to NTV Overlay. For example, an icon-based graphical user interface (GUI) may be used as long as it can be visually recognized that the still images of all the photoacoustic images are overlaid and displayed. A color of the NTV Overlay character is not particularly limited and can be randomly changed by the operator. The control unit 28 can also store the NTV Overlay image Io displayed on the upper side of the image display unit 30 in the storage unit 29 by an input from the input unit 40. In the case, the four thumbnail images displayed on the image display unit 30 may also be stored together.

Next, in a case where the cell of the subject is collected by the puncture needle 15, the collected cell is diagnosed. In a case where the syringe operator H presses the operation portion Sa, a collected cell C is sprayed on a surface of a glass preparation G from the tip opening 15e of the puncture needle 15 through the tube Sb as shown in FIG. 14. A date when the cell C is collected, the name of the patient, or the like is described in one end portion Ga of the surface of the preparation G. The preparation G on which the cell C is sprayed is stained, and then the user observes whether or not a cancer cell exists with a microscope or the like. In this manner, the series of pieces of processing of the FNA is performed.

With the ultrasound unit 12 according to the embodiment, the position information stored for each trigger is displayed on the image display unit 30 after the examination. Therefore, it is possible to accurately grasp the position of the tip portion of the puncture needle 15 on the photoacoustic image. That is, it is possible to accurately grasp where the puncture needle 15 punctures in the subject after the examination. Therefore, it can be used as evidence whether or not the puncture is appropriately performed.

Only the tip portions Nt of the puncture needle N are displayed on the NTV Overlay image Io in FIG. 13, but actually, a portion other than the tip portion Nt is also displayed. However, it is also possible to display only the detected tip portion Nt in a case where the positions of the puncture needle N and the tip portion Nt of the puncture needle N in the image are detected in the photoacoustic image. In this case, the detected tip portion Nt may be displayed as a marker.

Figure 15:
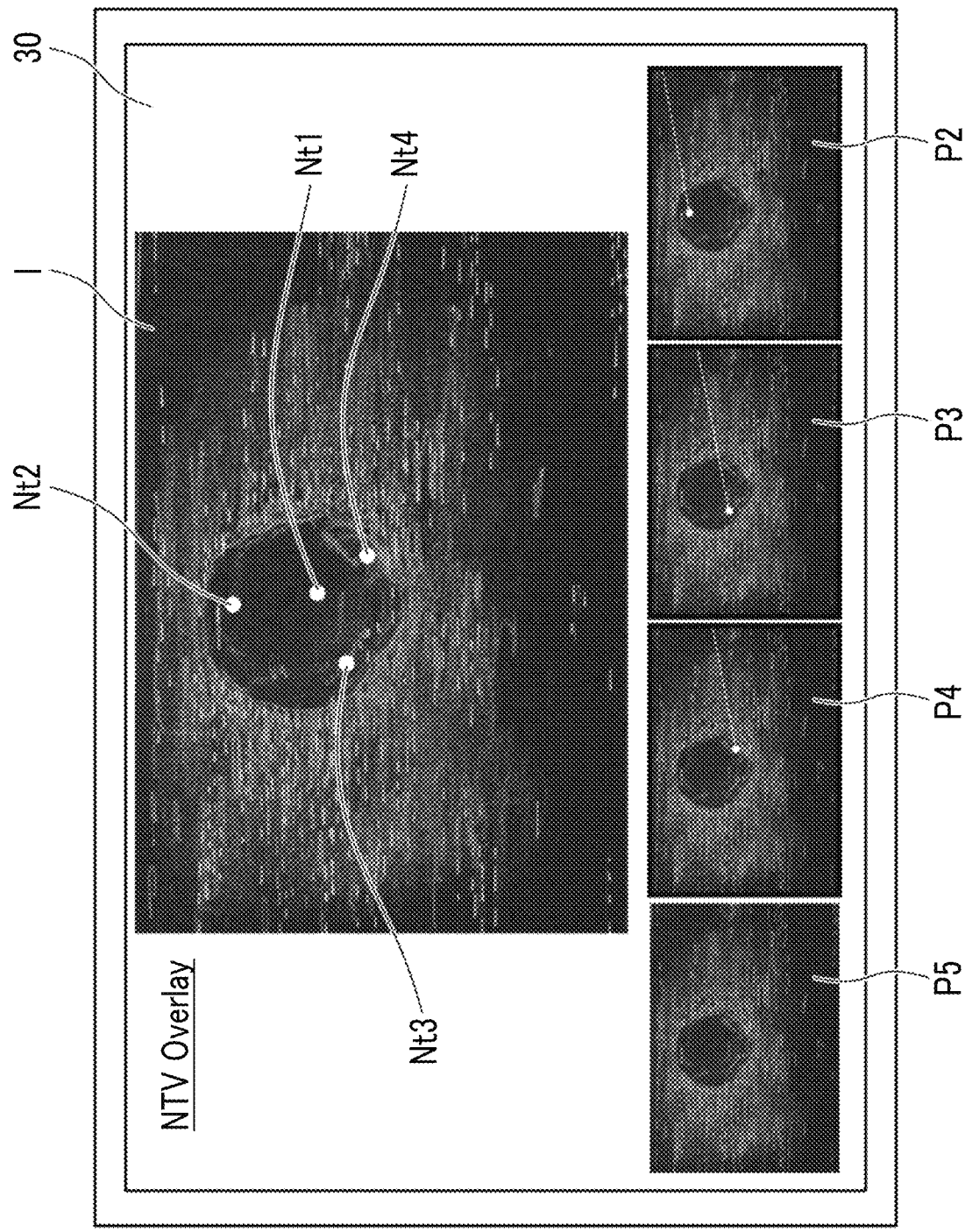
FIG. 15 is a view of an example of an NTV Overlay image and thumbnail images displayed on the image display unit (part 2).

The NTV Overlay image Io is not limited to the above embodiment, and the user can randomly select the still image of the photoacoustic image to be overlaid. In this case, in order to make the photoacoustic images used for the NTV Overlay image Io easier to understand, the control unit 28 displays frames of the thumbnail images P2 to P4 using the photoacoustic images used for the NTV Overlay image Io in a thick frame or in a different color frame as shown in FIG. 15. For example, an icon-based graphical user interface (GUI) may be used as long as the photoacoustic images used for the NTV Overlay image Io can be visually recognized. In FIG. 15, the thumbnail image P1 is also selected as the photoacoustic image used for the NTV Overlay image Io although the image is not displayed as a thumbnail on the image display unit 30. In the embodiment, the image display unit 30 is set to display four thumbnail images, and a thumbnail image stored first is not displayed in a case where a new thumbnail image is displayed. For example, any image can be displayed as the thumbnail image by the user operating a scroll (not shown). The number of thumbnail images that can be displayed on the image display unit 30 can be set by the user.

Figure 16:
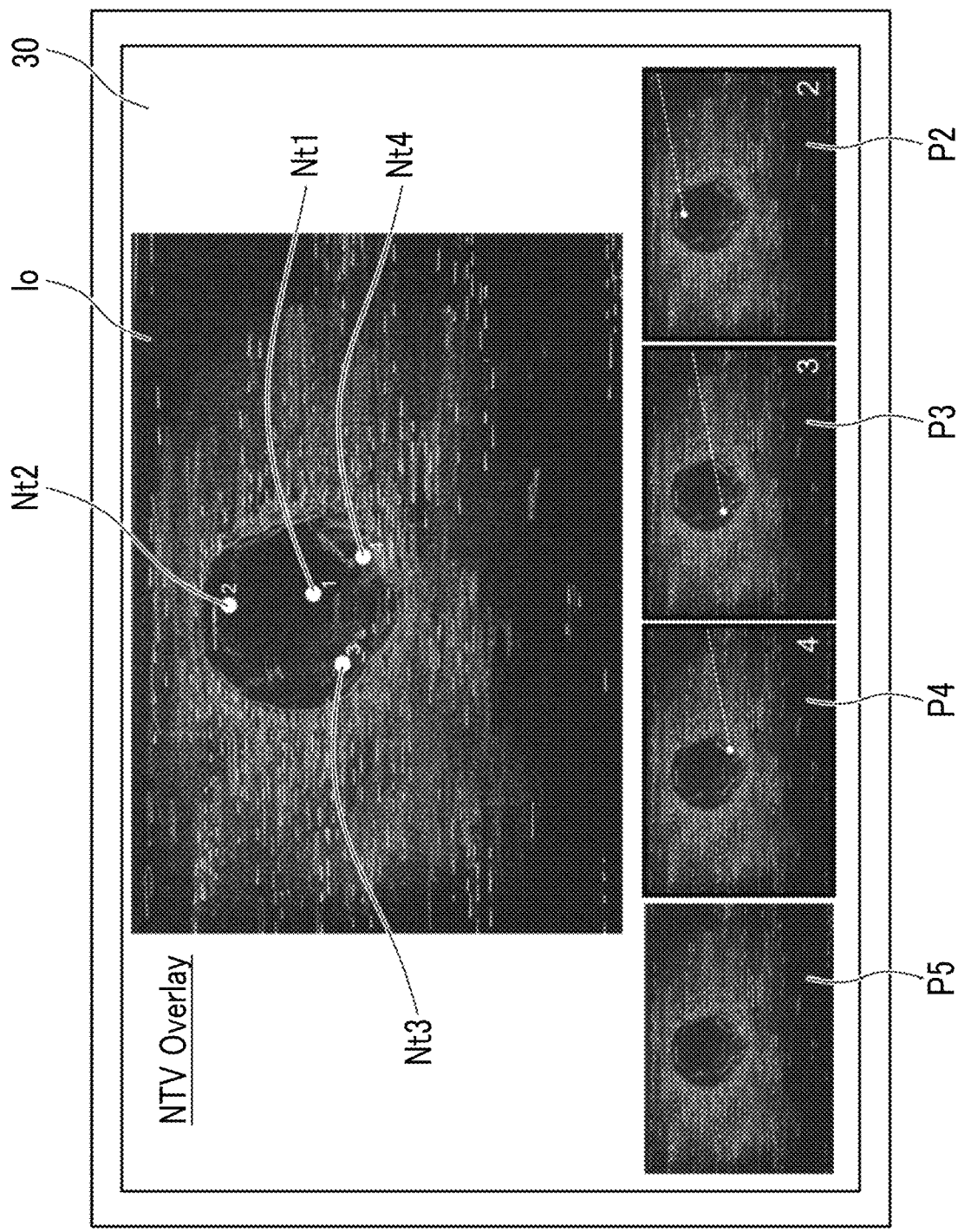
FIG. 16 is a view of an example of an NTV Overlay image and thumbnail images displayed on the image display unit (part 3).

As shown in FIG. 16, the control unit 28 may display the thumbnail images P1 to P4 (the thumbnail image P1 is assumed to be also selected although the image is not displayed on the image display unit 30) using the photoacoustic images used for the NTV Overlay image Io by respectively assigning numbers to the images, display the tip portions Nt of the puncture needle N on the NTV Overlay image Io as markers, and display the numbers corresponding to the thumbnail images P1 to P4 also near the respective markers. Accordingly, it is possible to easily identify the photoacoustic images used for the NTV Overlay image Io. A color of the marker and the number may be changed and displayed for each corresponding number. The color can be randomly changed by the user.

Figure 17:
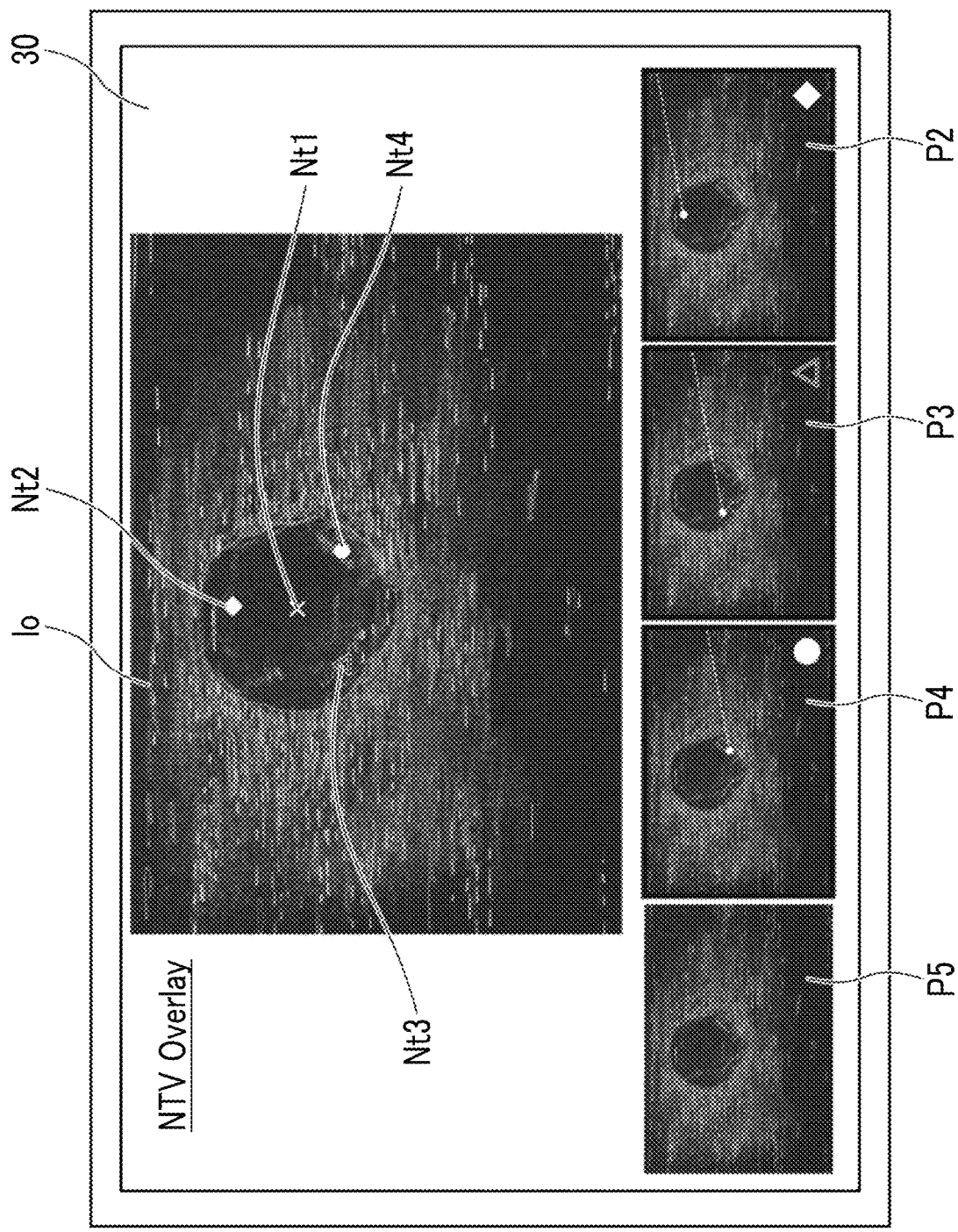
FIG. 17 is a view of an example of an NTV Overlay image and thumbnail images displayed on the image display unit (part 4).

As shown in FIG. 17, the control unit 28 may display the tip portions Nt of the puncture needle N on the NTV Overlay image Io with markers having different shapes and display the thumbnail images P1 to P4 (the thumbnail image P1 is assumed to be also selected although the image is not displayed on the image display unit 30) of the photoacoustic images used for the NTV Overlay image Io with the markers corresponding to the tip portions Nt of the puncture needle N on the NTV Overlay image Io.

Figure 18:
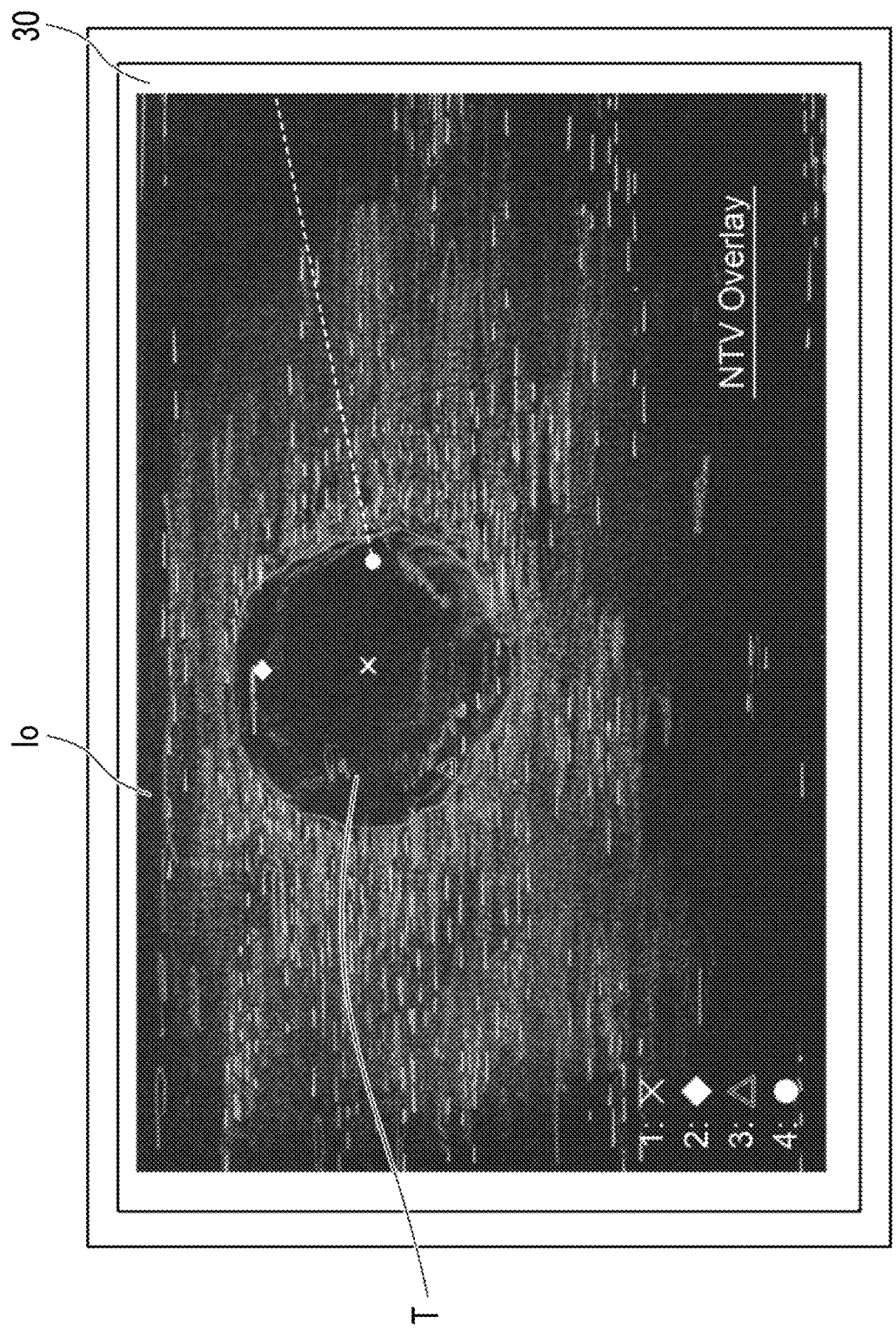
FIG. 18 is a view of an example of an NTV Overlay image displayed on the image display unit.

The thumbnail image may not be displayed depending on the size of the image display unit 30. In the case, it is not necessary to display the thumbnail image on the image display unit 30. In the case, for example, the control unit 28 may display the markers used in the overlaid image I in a stored order on the lower left of the image display unit 30 as shown in FIG. 18.

In the embodiment, the ultrasound image Ib (hereinafter referred to as a representative image) on which the still image of the photoacoustic image is overlaid is used as the image displayed on the image display unit 30 during the NTV Overlay display. The invention is not limited thereto. For example, an ultrasound image Ib initially saved during the NTV mode may be used as a default representative image. In this case, the representative image can be changed from the default image to any image by the user. The user may randomly change the representative image from the ultrasound images of the same patient stored in the photoacoustic image generation system 10 or a server (not shown).

In the embodiment, the NTV Overlay display is performed in the series of pieces of processing of the FNA. However, the invention is not limited thereto. After the series of pieces of processing of the FNA ends, for example, the control unit 28 can read out the representative image and the photoacoustic image stored in the storage unit 29 in an archived state, and overlay and display the images on the image display unit 30 through the image output unit 26.

In the embodiment, the NTV Overlay display is performed in a case where the NTV Overlay button is pressed. However, the invention is not limited thereto. The display may be automatically switched to the NTV Overlay display. Specifically, after the NTV mode is turned off in step S16 in FIG. 3 and then, for example, one or two seconds later, the control unit 28 may automatically switch the display to the NTV Overlay display. A switching time from the NTV mode being turned off to the NTV Overlay display may be set in advance by the user.

In the embodiment, the control unit 28 turns off the NTV mode in a case where the puncture needle 15 is determined to be removed from the subject. However, the invention is not limited thereto, and the NTV mode may be turned off automatically. Specifically, in a case where the control unit 28 determines that the tip portion Nt of the puncture needle N is no longer detected from the target region T displayed on the image display unit 30 and then, for example, 5 seconds elapse, the NTV mode may be turned off. As another embodiment, the NTV mode can be turned off in a case where the control unit 28 detects that the tip portion Nt of the puncture needle N existing in the target region T returns to a specific region set at a right end or a left end on the image display unit 30. The user may be able to set in advance the elapsed time after the tip portion Nt of the puncture needle N is determined to be no longer detected.

In the embodiment, the trigger signal is assumed to be input to the control unit 28 in a case where the save button is pressed, but the invention is not limited thereto. For example, it is assumed that the control unit 28 comprises a tip position detection function for detecting the position of the tip portion Nt of the puncture needle N based on the photoacoustic image generated by the photoacoustic image generation unit 24. As a detection method of the position of the tip portion Nt of the puncture needle N, for example, the position of the maximum brightness point in the photoacoustic image may be detected as the position of the tip portion Nt of the puncture needle N.

The control unit 28 may detect the movement of the tip portion Nt of the puncture needle N and generate a trigger signal based on the detection result. Specifically, the trigger signal may be generated in a case where the control unit 28 determines that the position of the tip portion Nt does not move more than a predetermined distance within a predetermined time. In this case, the control unit 28 calculates the total number of distances that the tip portion Nt moves at each predetermined time. In a case where the calculated value is equal to or less than the predetermined distance value, it is determined that the tip portion Nt of the puncture needle N does not move, that is, a cell is being collected and the control unit 28 may generate the trigger signal.

As still another embodiment, a trigger signal may be generated in a case where a direction in which the position of the tip portion Nt of the puncture needle N on the photoacoustic image changes over time is switched from one direction to another direction. Specifically, the position of the tip portion Nt of the puncture needle N on the photoacoustic image is detected in a time-series, a difference between current and past positions is taken, positive or negative of the difference is determined, and whether the needle moves toward the body or the outside of the body may also be a trigger. In this case, a direction from the upper right end portion to the upper left end portion of the photoacoustic image is set as a positive direction of the X-axis and a direction from the upper right end portion to the lower right end portion of the photoacoustic image is set as a positive direction of the Y-axis, assuming that the puncture needle N is inserted from a probe orientation side (upper right side toward the screen). The control unit 28 may generate the trigger signal by determining that the puncture needle 15 is punctured in a case where there is a positive value change from the past in any one of an X coordinate or a Y coordinate or the puncture needle 15 is removed in a case where there is a negative value change from the past in any one of the X coordinate or the Y coordinate. Alternatively, it may be determined that the puncture needle 15 is punctured in a case where there is a positive value change from the past in both the X coordinate and the Y coordinate or the puncture needle 15 is removed in a case where there is a negative value change from the past in both the X coordinate and the Y coordinate. An insertion position of the puncture needle N may be set in advance an insertion direction (for example, from the upper right side of the photoacoustic image), or a side where the tip portion Nt is first viewed on both the left and right sides of the photoacoustic image may be determined automatically as the insertion position.

Hereinafter, a second embodiment of a photoacoustic image generation apparatus according to the invention will be described in detail with reference to drawings. The photoacoustic image generation apparatus according to the embodiment can have the same configuration as that of the ultrasound unit 12 of the photoacoustic image generation system 10 in FIG. 1. Therefore, description thereof will be omitted, and only different portions will be described in detail.

Figure 19:
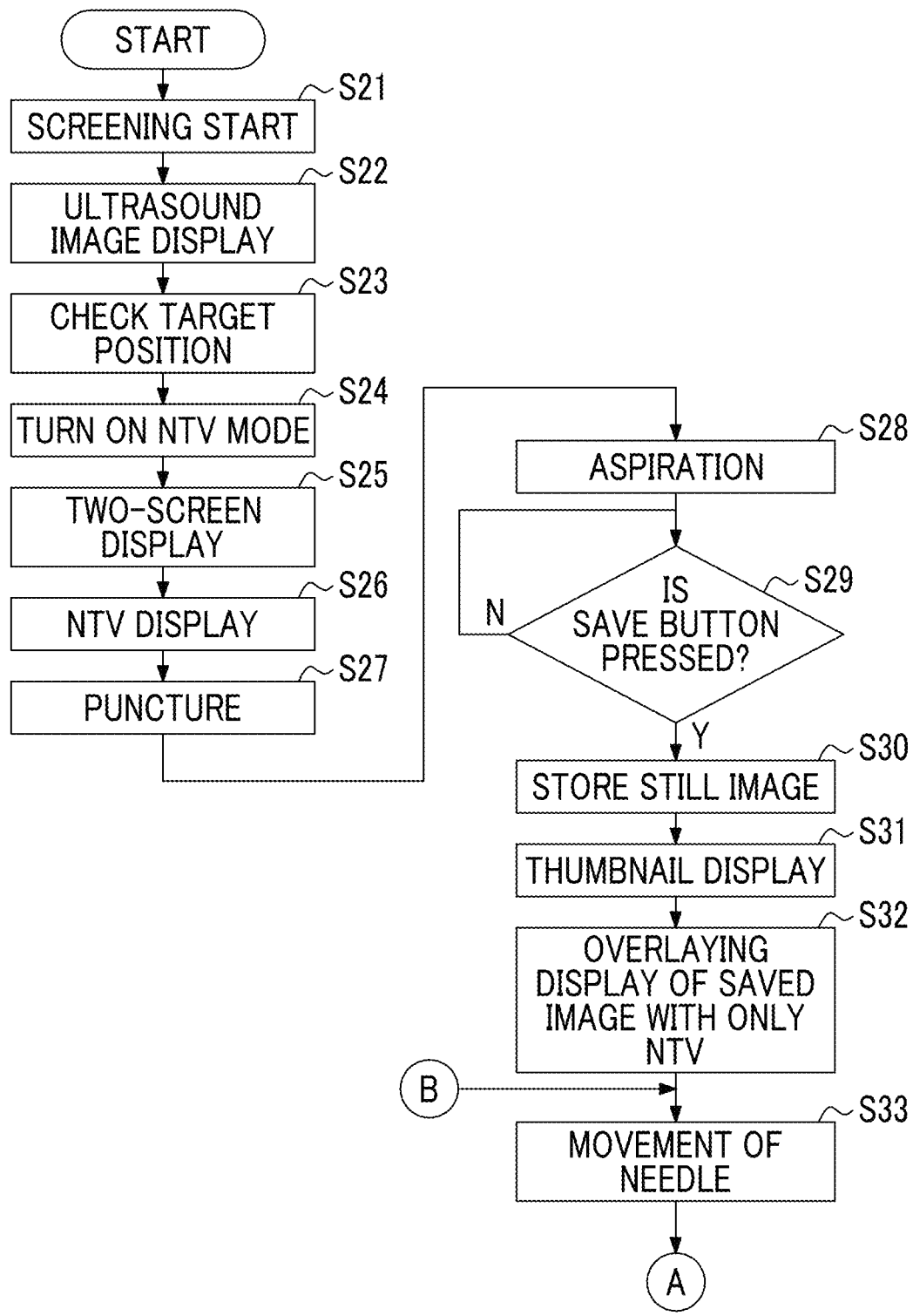
FIG. 19 is another flowchart of a series of pieces of processing of the FNA including an operation method of a photoacoustic image generation system (part 1).
Figure 20:
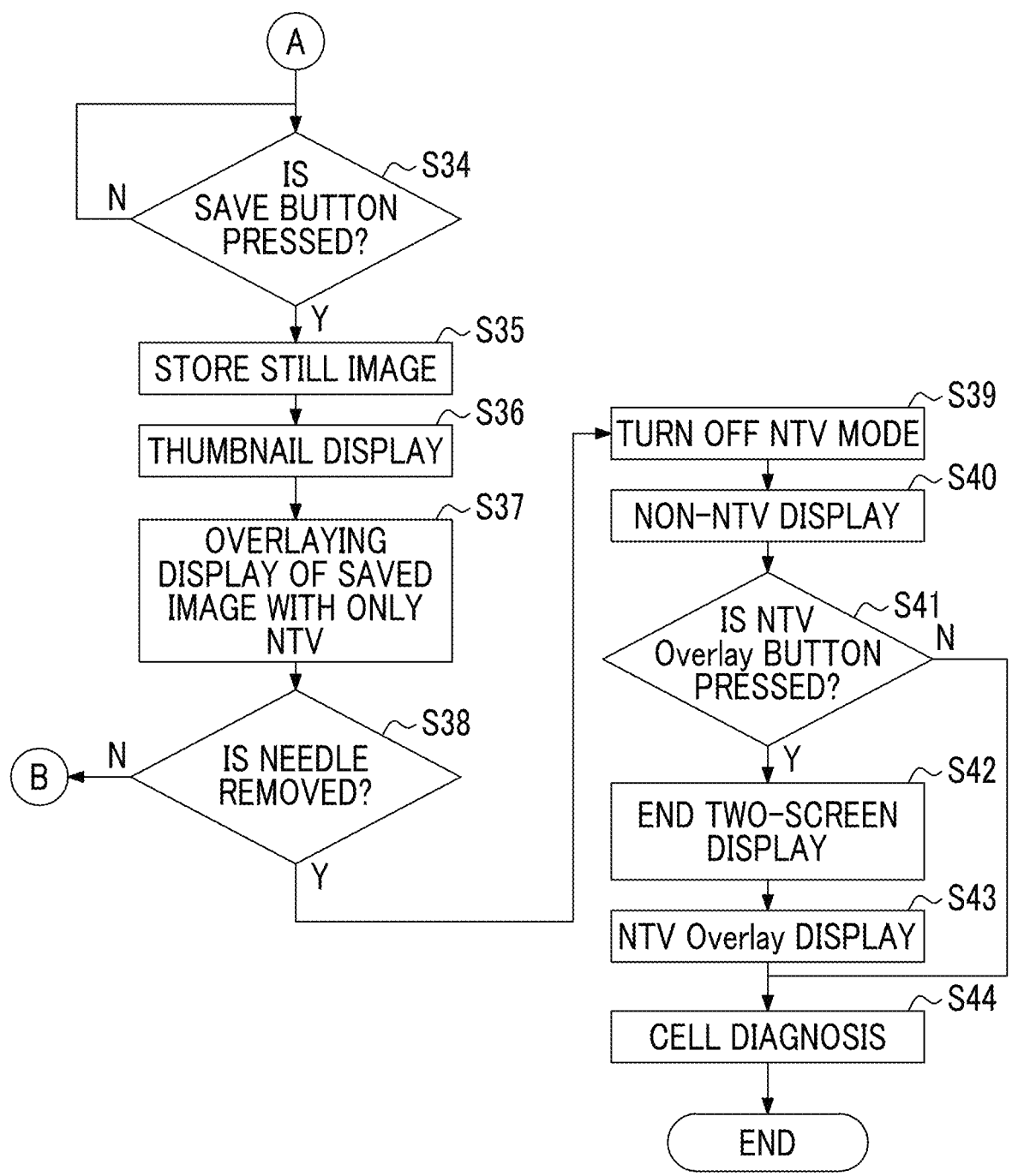
FIG. 20 is another flowchart of the series of pieces of processing of the FNA including the operation method of the photoacoustic image generation system (part 2).
Figure 21:
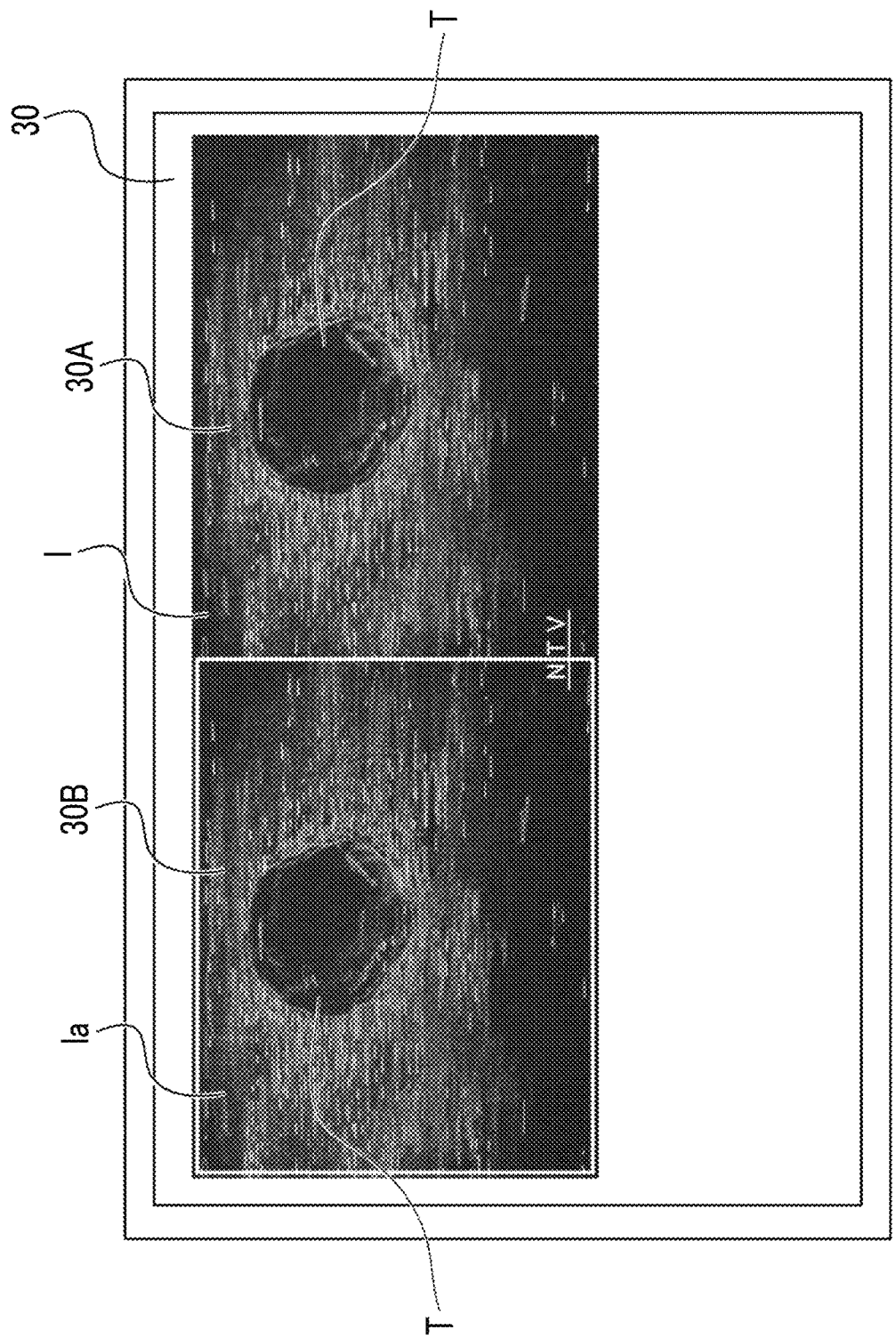
FIG. 21 is a view of an example of a two-screen display on the image display unit (part 1).
Figure 22:
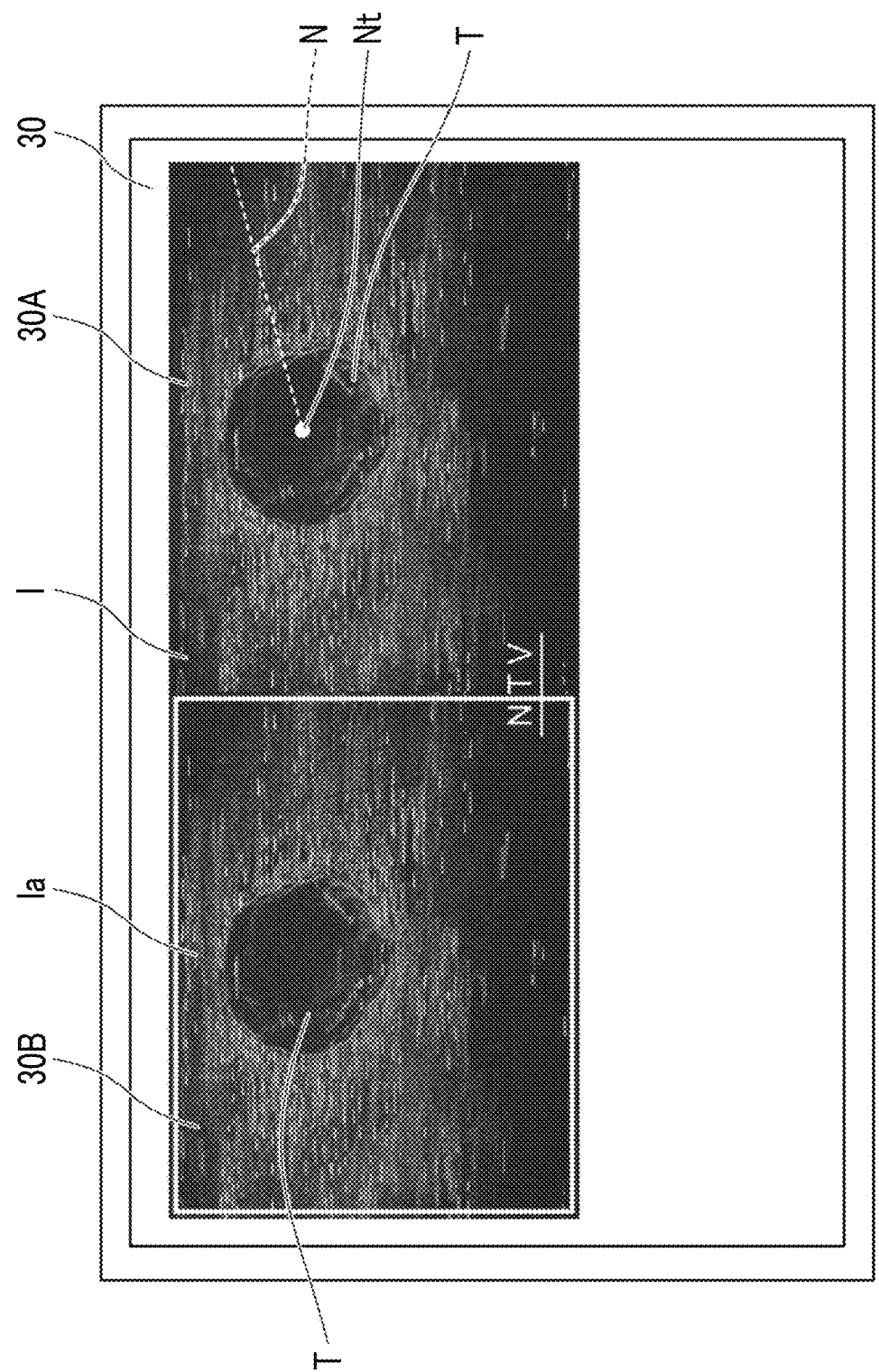
FIG. 22 is a view of an example of the two-screen display on the image display unit (part 2).

In the embodiment described above, the main image to be displayed on the image display unit 30, that is, the image except for the thumbnail image is one. However, a two-screen display is performed in the embodiment. Here, FIGS. 19 and 20 show flowcharts of a series of pieces of processing of the FNA including the operation method of the photoacoustic image generation system 10 comprising the ultrasound unit 12 according to the embodiment. Processing from steps S21 to S24 in FIG. 19 is the same as the processing from steps S1 to S4 in FIG. 3 and thus description thereof will be omitted here. FIGS. 21 and 22 show examples of the two-screen display in the image display unit, and FIGS. 23 to 28 show examples of the two-screen display and thumbnail images in the image display unit, respectively.

As shown in FIG. 19, in a case where the NTV mode is turned on (step S24), the control unit 28 performs the two-screen display on the image display unit 30 of a first display unit 30A on the right side of the screen and a second display unit 30B on the left side of the screen (step S25), and displays a character of NTV (step S26) as shown in FIG. 21. In the embodiment, the first display unit 30A displays an overlaid image I obtained by overlaying and combining a real-time photoacoustic image generated by the photoacoustic image generation unit 24 and a real-time ultrasound image Ib generated by the ultrasound image generation unit 25, and the second display unit 30B displays a representative image Ia. In the embodiment, the representative image Ia is assumed to be the ultrasound image Ib stored in the storage unit 29 by the control unit 28 at the timing when the NTV mode is turned on.

The invention is not limited thereto, and the representative image Ia may be an ultrasound image Ib stored in the storage unit 29 before the NTV is turned on, an ultrasound image Ib acquired in the past, or an image acquired at any timing as long as the image is obtained by capturing the same site of the same patient. The image is not limited to a still image and may be a video. The video may be displayed by repeatedly reproducing a video captured for a certain period of time. The video may be an image in which a color Doppler image is overlaid on a B-mode image. In general, in a case where the puncture needle 15 is inserted into a subject, it is desired to avoid a blood vessel. On the contrary, since blood information can be visually recognized by displaying the color Doppler image, it is possible for the user to easily avoid the blood vessel.

The representative image Ia may be a real-time ultrasound image Ib generated by the ultrasound image generation unit 25. The representative image Ia may be volume data such as a three-dimensional image or a four-dimensional image (a real-time video of a three-dimensional image). In this case, a two-dimensional probe or a mechanical probe is used as the ultrasound probe 11. A cross-sectional image in the longitudinal direction and a cross-sectional image in the transverse direction may be disposed on the left and right or top and bottom as the representative image Ia. In this case, the image display unit 30 displays three images of the cross-sectional image in the longitudinal direction, the cross-sectional image in the transverse direction, and the overlaid image I. The first display unit 30A and the second display unit 30B may be disposed opposite to each other. The first display unit 30A and the second display unit 30B may also be disposed side by side in the vertical direction. Since the display of the first display unit 30A is the same as the display method of the overlaid image I in the embodiment described above, detailed description thereof is omitted here.

in a case where the first display unit 30A of the image display unit 30 performs the NTV display (step S26), the user punctures the subject with the puncture needle 15 at any timing such as before and after driving the laser unit 13 (step S27) and the puncture needle 15 is inserted into the subject. In a case where the puncture needle 15 is inserted into the subject, the puncture needle N and the tip portion Nt of the puncture needle N are displayed on the overlaid image I as shown in FIG. 22. In a case where the tip portion Nt of the puncture needle N reaches the target region T on the overlaid image I, the user aspirates a cell inside the target region T from the tip opening 15e of the puncture needle 15 as described above (step S28).

Next, the control unit 28 determines whether or not a trigger signal is input from the input unit 40 to determine whether or not the save button is pressed during the aspiration of the cell (step S29). In a case where the save button is determined to be not pressed (step S29; N), the control unit 28 repeatedly performs the processing of step S29 until the save button is pressed. On the other hand, in a case where the save button is determined to be pressed (step S29; Y), the control unit 28 stores a still image of the overlaid image I in the storage unit 29 (step S30). In the case, the photoacoustic image constituting the overlaid image I is also stored in the storage unit 29 as position information of the tip portion Nt of the puncture needle N. The ultrasound image constituting the overlaid image I is also stored in the storage unit 29. The position of the maximum brightness point in the photoacoustic image is detected as the position of the tip portion Nt of the puncture needle N, and a photoacoustic image on which only NTV is displayed is also stored.

Figure 23:
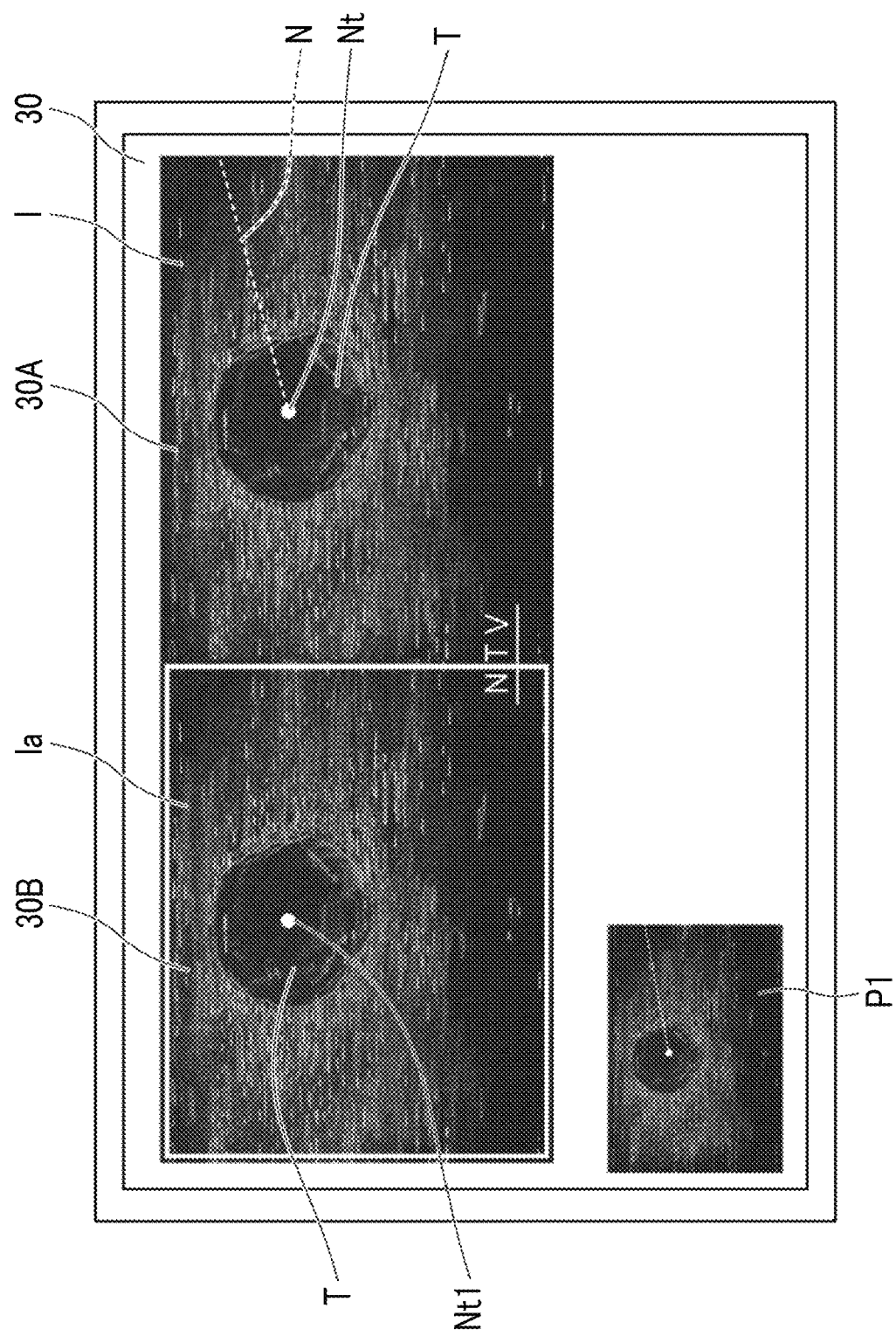
FIG. 23 is a view of an example of the two-screen display and a thumbnail image on the image display unit (part 1).

As shown in FIG. 23, the control unit 28 displays the overlaid image I stored in the storage unit 29 as a thumbnail on the image display unit 30 (step S31). In the embodiment, the control unit 28 displays the thumbnail image P1 at the lower left of the image display unit 30, that is, below the second display unit 30B.

Figure 24:
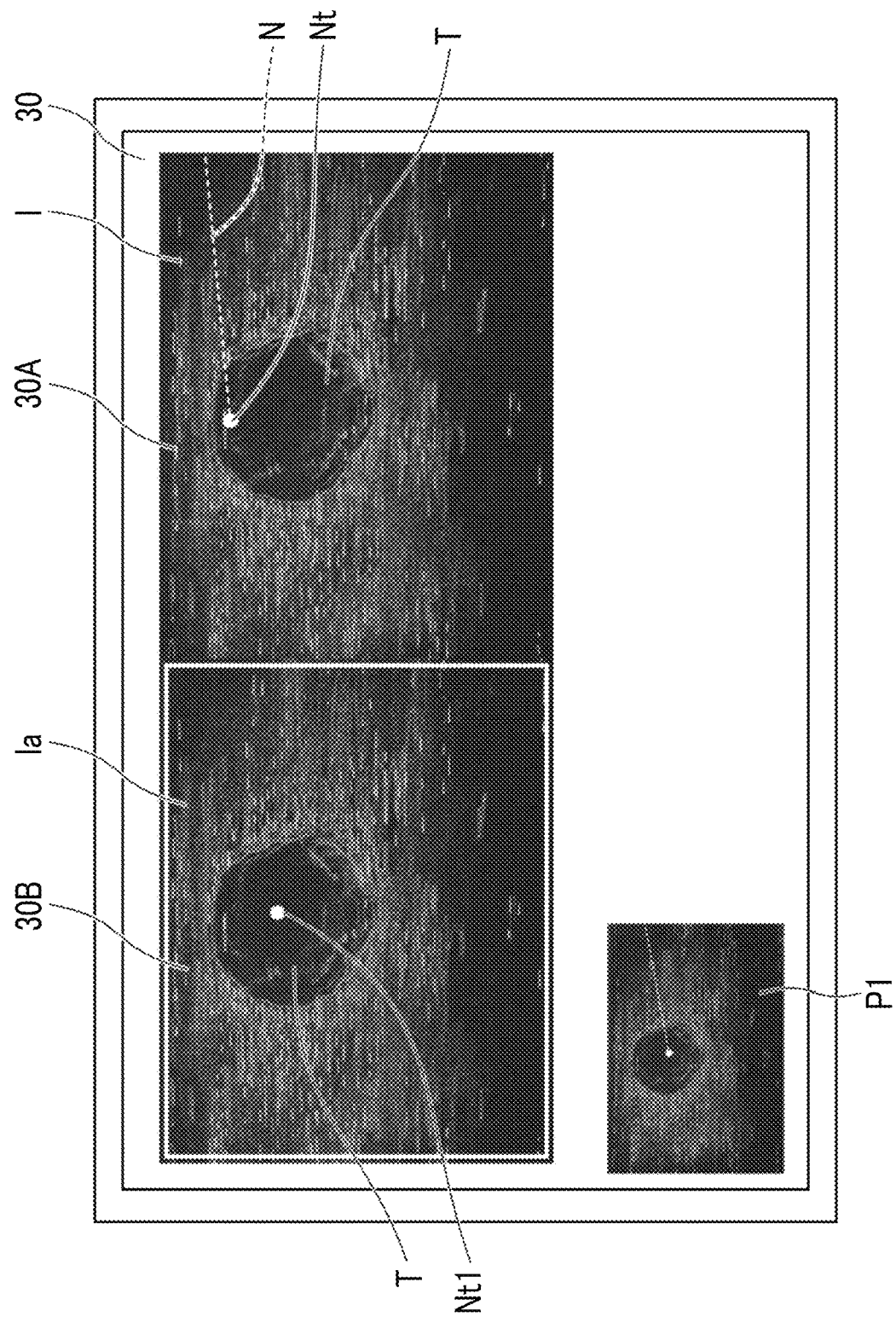
FIG. 24 is a view of an example of the two-screen display and a thumbnail image on the image display unit (part 2).

As shown in FIG. 23, the control unit 28 overlays and displays the photoacoustic image on which only the NTV is displayed and stored in the storage unit 29 on the representative image Ia (step S32). Next, as shown in FIG. 24, the user moves the puncture needle 15 to another position in the target region T (step S33). In the embodiment, the puncture needle 15 is moved while the aspiration is performed by the syringe S in a state where the puncture needle 15 is inserted into the subject.

Next, the control unit 28 shifts the processing to A of FIG. 20, and the control unit 28 determines whether or not the save button is pressed as shown in FIG. 20 (step S34). In a case where the save button is determined to be not pressed (step S34; N), the control unit 28 repeatedly performs the processing of step S34 until the save button is pressed. On the other hand, in a case where the save button is determined to be pressed (step S34; Y), the control unit 28 causes the storage unit 29 to store the still image of the overlaid image I after the movement of the puncture needle 15 (step S35). In the case, the photoacoustic image constituting the overlaid image I after movement is stored as the position information of the tip portion Nt of the puncture needle N. The position of the maximum brightness point in the photoacoustic image is detected as the position of the tip portion Nt of the puncture needle N, and the photoacoustic image with only the NTV is also stored.

Figure 25:
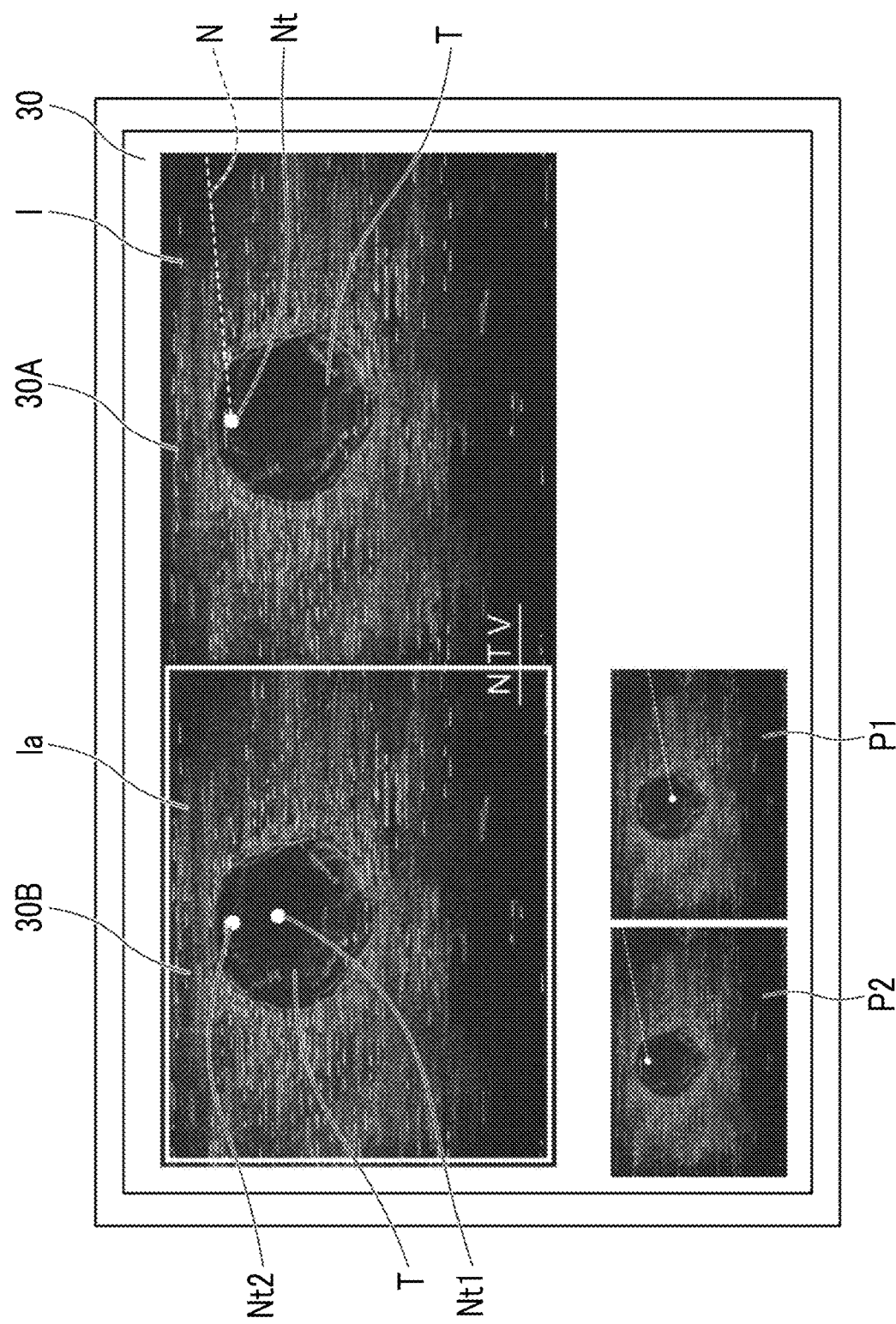
FIG. 25 is a view of an example of the two-screen display and thumbnail images on the image display unit (part 3).

As shown in FIG. 25, the control unit 28 causes the image display unit 30 to display the overlaid image I after the movement stored in the storage unit 29 as a thumbnail (step S36). The control unit 28 displays a thumbnail image P2 of the overlaid image I stored this time on the left side of the thumbnail image P1 of the overlaid image I stored last time. A display order of the thumbnails can be set in advance by the user. In the embodiment, the display is performed such that the last stored thumbnail image of the overlaid image I is displayed at the left end. Next, as illustrated in FIG. 25, the control unit 28 overlays and displays the photoacoustic image with only the NTV stored in the storage unit 29 on the representative image Ia (step S37).

Figure 26:
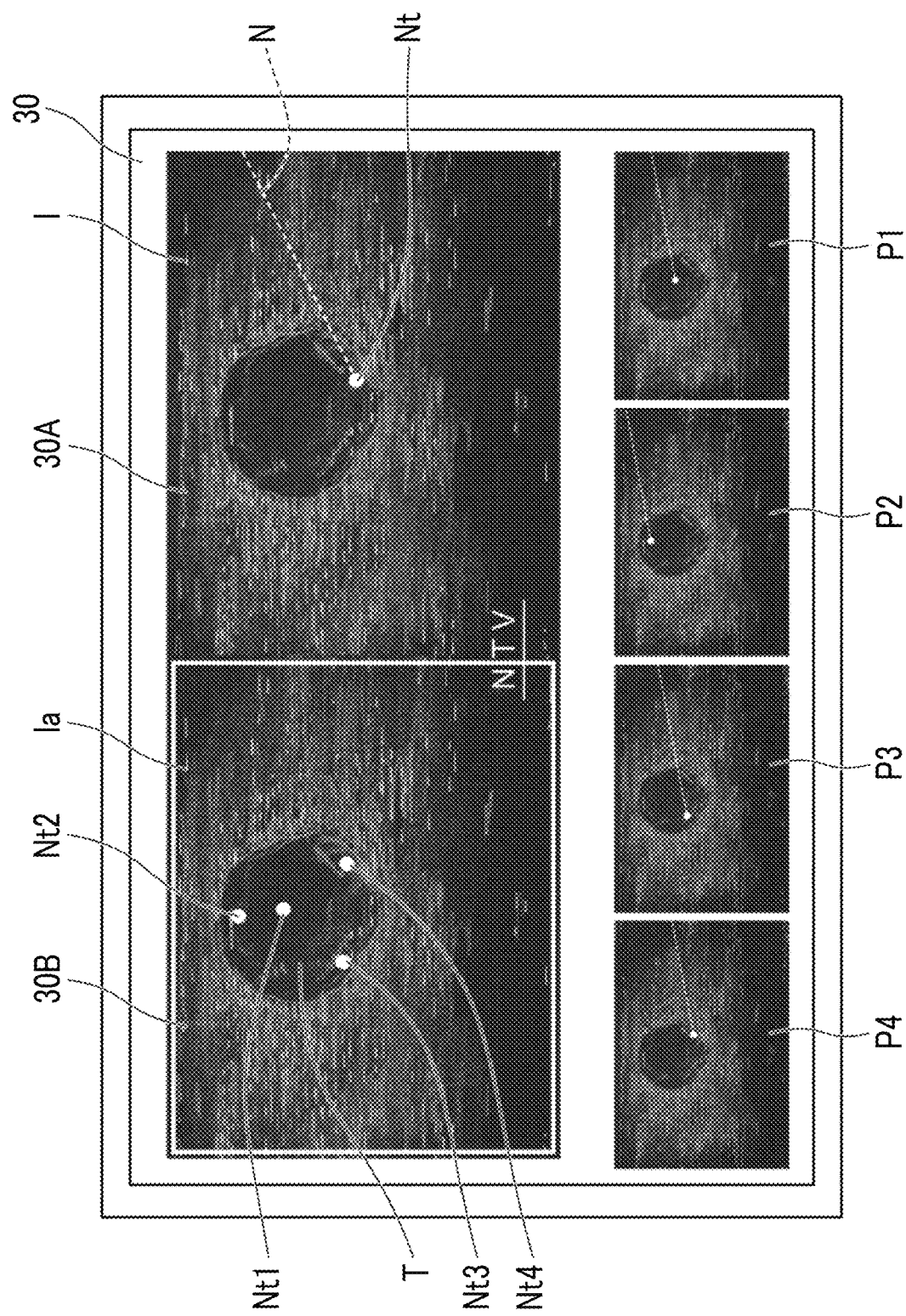
FIG. 26 is a view of an example of the two-screen display and thumbnail images on the image display unit (part 4).

Next, the control unit 28 determines whether or not the puncture needle 15 is removed from the subject (step S38). In a case where the puncture needle 15 is determined to be not removed (step S38; N), the control unit 28 shifts the processing to B. That is, the control unit 28 shifts the processing to step S33 in FIG. 19 and repeats subsequent processing. In the embodiment, the pieces of processing of steps S33 to S38 are repeated three times, and the control unit 28 displays four thumbnail images P1 to P4 as shown in FIG. 26. In the embodiment, four pieces of position information of the tip portion Nt of the puncture needle N are acquired assuming that the user collects cells at four locations in the target region T. However, the invention is not limited thereto. Five or six pieces of position information of the tip portion Nt are acquired in a case where cells are collected at five or six locations. Ten pieces of position information of the tip portion Nt are acquired in a case where cells are collected at ten locations. The locations where the cells are collected vary depending on a type, size, or the like of the target, but the position information of the tip portion Nt is acquired at all locations where the cells are collected in the invention.

Figure 27:
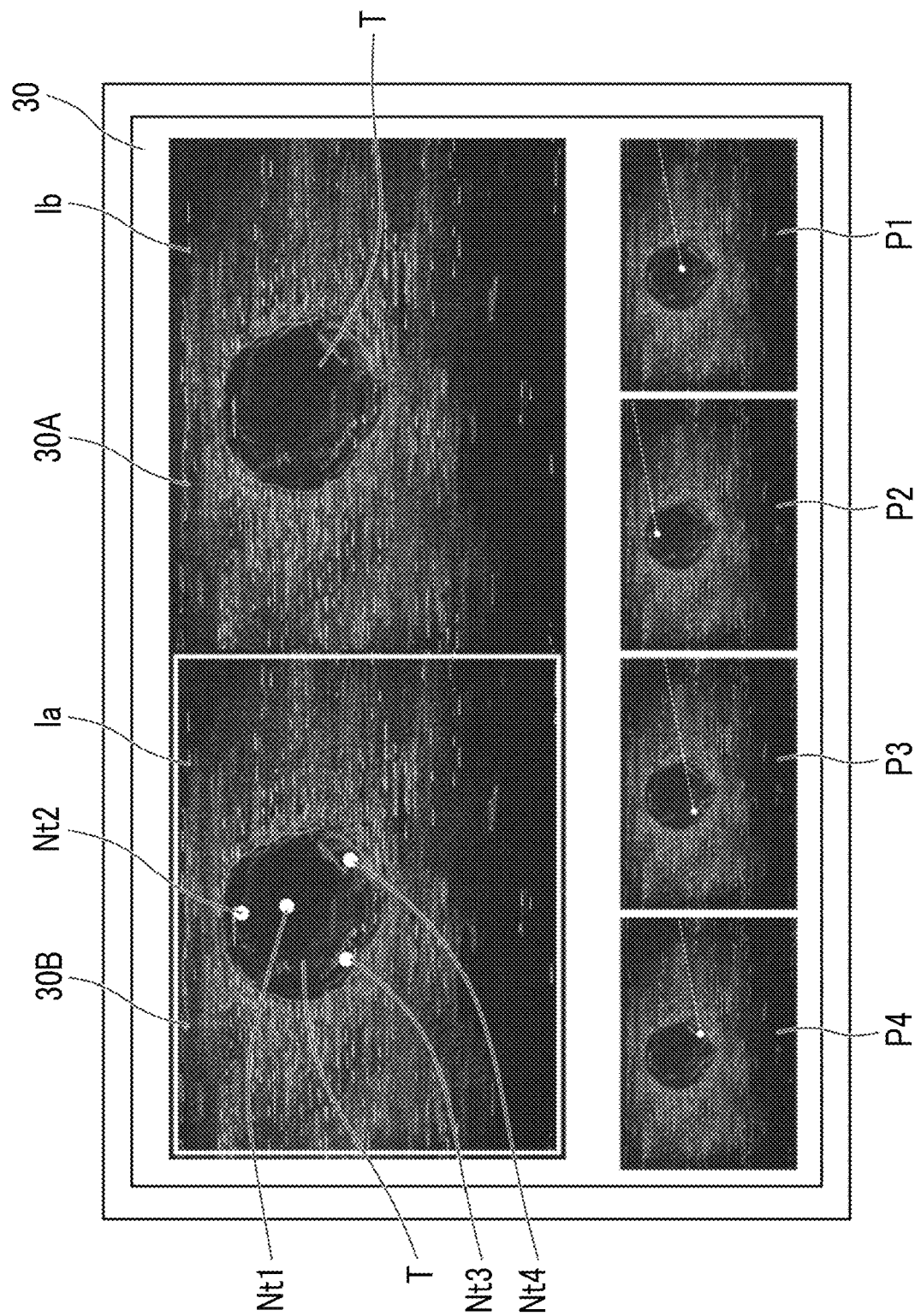
FIG. 27 is a view of an example of the two-screen display and thumbnail images on the image display unit (part 5).

On the other hand, in a case where the control unit 28 determines in step S38 that the puncture needle 15 is removed (step S38; Y), the control unit 28 turns off the NTV mode (step S39) and does not display the NTV character on the image display unit 30 through the image output unit 26 as shown in FIG. 27 (step S40). That is, on the image display unit 30, only the real-time image of the ultrasound image Ib is displayed on the first display unit 30A, the representative image Ia and the photoacoustic image with only the NTV for the number of times the save button is pressed are overlaid and displayed on the second display unit 30B, and the thumbnail images P1 to P4 of the overlaid image I stored in the storage unit 29 are displayed below the first display unit 30A and the second display unit 30B as shown in FIG. 27.

The control unit 28 determines whether or not the NTV Overlay button is pressed (step S41). In a case where the control unit 28 determines that the NTV Overlay button is not pressed (step S41; N), the collected cell is diagnosed as described below (step S44) and the series of pieces of processing ends. On the other hand, in a case where the NTV Overlay button is determined to be pressed (step S41; Y), the control unit 28 ends the two-screen display by the image display unit 30 (step S42), displays only the image and the thumbnail images displayed on the second display unit 30B on the image display unit 30, and displays the character of NTV Overlay on the screen (step S43) as shown in FIG. 28. In the embodiment, this display is referred to as an NTV Overlay display, and the displayed image is referred to as the NTV Overlay image Io. It is possible to store the image on which the image and the thumbnail images displayed on the second display unit 30B are displayed in the storage unit 29. It is possible for the user to randomly select the image stored in the storage unit 29.

With the ultrasound unit 12 according to the embodiment, the position information stored for each trigger is displayed on the image display unit 30 after the examination. Therefore, it is possible to accurately grasp the position of the tip portion of the puncture needle 15 on the photoacoustic image. That is, it is possible to grasp all positions where the puncture needle 15 punctures in the subject after the examination. Therefore, it can be used as evidence whether or not the puncture is appropriately performed. The movement of the puncture needle 15 can be confirmed with a real-time image and the position where the previous puncture needle 15 is punctured can be confirmed. Therefore, it is possible to prevent the same position from being punctured.

An acoustic wave diagnostic apparatus according to the embodiment of the invention is not limited to the above embodiments and can be changed as appropriate without departing from the spirit of the invention.

EXPLANATION OF REFERENCES

10: photoacoustic image generation system
11: ultrasound probe
12: ultrasound unit (photoacoustic image generation apparatus)
13: laser unit
15: puncture needle
15a: puncture needle main body
15b: optical fiber
15c: photoacoustic wave generation portion
15d: hollow portion
15e: tip opening
16: optical cable
21: receiving circuit
22: receiving memory
23: data demultiplexing unit
24: photoacoustic image generation unit
25: ultrasound image generation unit
26: image output unit
27: transmission control circuit
28: control unit
29: storage unit
30: image display unit
30A: first display unit
30B: second display unit
40: input unit
C: cell
G: preparation
Ga: one end portion
H1: left hand
H2: right hand
H: syringe operator
I: overlaid image
Ia: representative image
Ib: ultrasound image
Io: NTV Overlay image
N: puncture needle
Nt: tip portion
P1: thumbnail image
P2: thumbnail image

What is claimed is:

1. A photoacoustic image generation apparatus comprising:
    a processor configured to:
        generate a photoacoustic image based on a detection signal acquired by detecting a photoacoustic wave emitted from a tip portion of an insert including a fine needle having a diameter of less than 1.4 mm inserted into a subject using an ultrasound probe;
        respond to a predetermined trigger to cause storage to store position information of the tip portion on the photoacoustic image for each trigger during a step of collecting a cell of the subject at the tip portion of the insert in cytology;
        display an ultrasound image based on a detection signal acquired by detecting a reflected acoustic wave with respect to an ultrasonic wave output into the subject using the ultrasound probe;
        display an overlaid image obtained by overlaying the ultrasound image and the photoacoustic image in real time to visualize the position of the tip portion; and
        display an accumulated image of the position information stored for each trigger, in case where the displaying of the overlaid image is off or plurality of overlaid images are saved by an user.

2. The photoacoustic image generation apparatus according to claim 1, further comprising:
    an user interface to which the predetermined trigger is input.

3. The photoacoustic image generation apparatus according to claim 1,
    wherein the processor generates the predetermined trigger in a case where a position of the tip portion on the photoacoustic image does not move more than a predetermined distance within a predetermined time.

4. The photoacoustic image generation apparatus according to claim 1,
    wherein the processor generates the predetermined trigger in a case where a direction in which a position of the tip portion on the photoacoustic image changes over time is switched from one direction to another direction.

5. The photoacoustic image generation apparatus according to claim 1,
    wherein the processor assigns identification information to the position information stored for each trigger.

6. The photoacoustic image generation apparatus according to claim 2,
    wherein the processor assigns identification information to the position information stored for each trigger.

7. The photoacoustic image generation apparatus according to claim 3,
    wherein the processor assigns identification information to the position information stored for each trigger.

8. The photoacoustic image generation apparatus according to claim 4,
    wherein the processor assigns identification information to the position information stored for each trigger.

9. The photoacoustic image generation apparatus according to claim 1, further comprising:
    a processor that generates an ultrasound image based on a detection signal acquired by detecting a reflected acoustic wave with respect to an ultrasonic wave output into the subject using the ultrasound probe; and
    an image display that displays at least one of the photoacoustic image or the ultrasound image,
    wherein the image display is able to perform a two-screen display, and
    wherein the processor displays the overlaid image obtained by overlaying the ultrasound image and the photoacoustic image in real time on one screen of the image display and displays a representative image on the other screen.

10. The photoacoustic image generation apparatus according to claim 2, further comprising:
    a processor that generates an ultrasound image based on a detection signal acquired by detecting a reflected acoustic wave with respect to an ultrasonic wave output into the subject using the ultrasound probe; and
    an image display that displays at least one of the photoacoustic image or the ultrasound image,
    wherein the image display is able to perform a two-screen display, and wherein the processor displays the overlaid image obtained by overlaying the ultrasound image and the photoacoustic image in real time on one screen of the image display and displays a representative image on the other screen.

11. The photoacoustic image generation apparatus according to claim 3, further comprising:
a processor that generates an ultrasound image based on a detection signal acquired by detecting a reflected acoustic wave with respect to an ultrasonic wave output into the subject using the ultrasound probe; and
an image display that displays at least one of the photoacoustic image or the ultrasound image,
wherein the image display is able to perform a two-screen display, and
wherein the processor displays the overlaid image obtained by overlaying the ultrasound image and the photoacoustic image in real time on one screen of the image display and displays a representative image on the other screen.

12. The photoacoustic image generation apparatus according to claim 4, further comprising:
a processor that generates an ultrasound image based on a detection signal acquired by detecting a reflected acoustic wave with respect to an ultrasonic wave output into the subject using the ultrasound probe; and
an image display that displays at least one of the photoacoustic image or the ultrasound image,
wherein the image display is able to perform a two-screen display, and
wherein the processor displays the overlaid image obtained by overlaying the ultrasound image and the photoacoustic image in real time on one screen of the image display and displays a representative image on the other screen.

13. The photoacoustic image generation apparatus according to claim 9,
wherein the representative image is a cross-sectional image in a longitudinal direction and a cross-sectional image in a transverse direction, and
wherein the processor causes the image display to display the cross-sectional image in the longitudinal direction and the cross-sectional image in the transverse direction side by side.

14. The photoacoustic image generation apparatus according to claim 1,
wherein the processor outputs the accumulated image of the position information stored for each trigger to an image display.

15. The photoacoustic image generation apparatus according to claim 2,
wherein the processor outputs an accumulated image of the position information stored for each trigger to an image display.

16. The photoacoustic image generation apparatus according to claim 3,
wherein the processor outputs an accumulated image of the position information stored for each trigger to an image display.

17. The photoacoustic image generation apparatus according to claim 1,
wherein the insert has an opening portion at a tip of the tip portion, and
wherein the processor causes the storage to store the position information in response to the predetermined trigger during a step of aspirating and collecting the cell of the subject from the opening portion.

18. The photoacoustic image generation apparatus according to claim 2,
wherein the insert has an opening portion at a tip of the tip portion, and
wherein the processor causes the storage to store the position information in response to the predetermined trigger during a step of aspirating and collecting the cell of the subject from the opening portion.

19. The photoacoustic image generation apparatus according to claim 3,
wherein the insert has an opening portion at a tip of the tip portion, and
wherein the processor causes the storage to store the position information in response to the predetermined trigger during a step of aspirating and collecting the cell of the subject from the opening portion.

20. A method of operating a photoacoustic image generation apparatus including a processor, the method comprising:
generating a photoacoustic image based on a detection signal acquired by detecting a photoacoustic wave emitted from a tip portion of an insert including a fine needle having a diameter of less than 1.4 mm inserted into a subject by the processor using an ultrasound probe;
responding to a predetermined trigger to cause storage to store position information of the tip portion on the photoacoustic image for each trigger by the processor during a step of collecting a cell of the subject at the tip portion of the insert in cytology;
display an ultrasound image based on a detection signal acquired by detecting a reflected acoustic wave with respect to an ultrasonic wave output into the subject using the ultrasound probe;
display an overlaid image obtained by overlaying the ultrasound image and the photoacoustic image in real time to visualize the position of the tip portion; and
display an accumulated image of the position information stored for each trigger, in case where the displaying of the overlaid image is off or plurality of overlaid images are saved by an user.

* * * * *